United States Patent
Kuroda et al.

(10) Patent No.: US 10,730,189 B2
(45) Date of Patent: Aug. 4, 2020

(54) CONTROL APPARATUS, CONTROL METHOD, AND MEDICAL SUPPORT ARM APPARATUS

(71) Applicant: SONY CORPORATION, Tokyo (JP)

(72) Inventors: Yohei Kuroda, Tokyo (JP); Tetsuharu Fukushima, Tokyo (JP); Fumiyasu Suzuki, Saitama (JP); Toshimitsu Tsuboi, Tokyo (JP)

(73) Assignee: SONY CORPORATION, Tokyo (JP)

( * ) Notice: Subject to any disclaimer, the term of this patent is extended or adjusted under 35 U.S.C. 154(b) by 263 days.

(21) Appl. No.: 15/745,173

(22) PCT Filed: May 31, 2016

(86) PCT No.: PCT/JP2016/066001
§ 371 (c)(1),
(2) Date: Jan. 16, 2018

(87) PCT Pub. No.: WO2017/022310
PCT Pub. Date: Feb. 9, 2017

(65) Prior Publication Data
US 2018/0264655 A1 Sep. 20, 2018

(30) Foreign Application Priority Data

Aug. 4, 2015 (JP) .................................. 2015-154100

(51) Int. Cl.
*A61B 1/32* (2006.01)
*B25J 13/08* (2006.01)
(Continued)

(52) U.S. Cl.
CPC .......... *B25J 13/085* (2013.01); *A61B 1/00006* (2013.01); *A61B 1/00149* (2013.01);
(Continued)

(58) Field of Classification Search
CPC .......... B25J 13/085; B25J 9/16; A61B 34/30; A61B 1/00149; A61B 90/50; A61B 1/00006; A61B 90/35; A61B 2090/508; A61B 2090/066
See application file for complete search history.

(56) References Cited

U.S. PATENT DOCUMENTS

| 4,989,161 A * | 1/1991 | Oaki | ................... B25J 9/1641 |
| | | | 700/261 |
| 8,864,846 B2 * | 10/2014 | Herr | ......................... A61F 2/66 |
| | | | 623/25 |

(Continued)

FOREIGN PATENT DOCUMENTS

| JP | 63-212483 A | 9/1988 |
| JP | 5-138583 A | 6/1993 |

(Continued)

OTHER PUBLICATIONS

International Search Report dated Sep. 6, 2016 in PCT/JP2016/066001.

*Primary Examiner* — Masud Ahmed
(74) *Attorney, Agent, or Firm* — Xsensus LLP

(57) ABSTRACT

[Object] To enable further suppression of the movement amount of an arm section when switching states.
[Solution] There is provided a control apparatus configured to execute a current tracking control on a basis of a measurement value of a torque sensor of an actuator provided in at least one of multiple joint sections included in an arm section of a medical support arm apparatus, the current tracking control causing a motor of the actuator to output torque by which a position and an attitude of the arm section are maintained, and switch a first state in which the motor is driven in accordance with a predetermined control method, and a second state in which the joint section is locked using a brake of the actuator.

18 Claims, 12 Drawing Sheets

(51) Int. Cl.
  *A61B 34/30* (2016.01)
  *A61B 1/00* (2006.01)
  *A61B 90/50* (2016.01)
  *A61B 90/35* (2016.01)
  *A61B 90/00* (2016.01)
  *B25J 9/16* (2006.01)

(52) U.S. Cl.
  CPC .............. *A61B 34/30* (2016.02); *A61B 90/50* (2016.02); *A61B 90/35* (2016.02); *A61B 2090/066* (2016.02); *A61B 2090/508* (2016.02); *B25J 9/16* (2013.01)

(56) References Cited

U.S. PATENT DOCUMENTS

| | | | | |
|---|---|---|---|---|
| 9,841,749 | B2* | 12/2017 | Linnell | G05B 19/409 |
| 2003/0055410 | A1* | 3/2003 | Evans | A61B 34/32 |
| | | | | 606/1 |
| 2008/0009771 | A1* | 1/2008 | Perry | B25J 9/0006 |
| | | | | 600/587 |
| 2010/0081886 | A1* | 4/2010 | Komuro | A61B 1/00149 |
| | | | | 600/229 |
| 2013/0204465 | A1* | 8/2013 | Phillips | G05D 1/0033 |
| | | | | 701/2 |
| 2014/0000355 | A1* | 1/2014 | Shikagawa | G01M 13/00 |
| | | | | 73/118.01 |
| 2017/0007336 | A1* | 1/2017 | Tsuboi | B25J 9/1674 |
| 2017/0080574 | A1* | 3/2017 | Kuroda | B25J 9/1641 |
| 2017/0341232 | A1* | 11/2017 | Perplies | A61G 12/002 |

FOREIGN PATENT DOCUMENTS

| | | |
|---|---|---|
| JP | 6-31656 A | 2/1994 |
| JP | 2007-301691 A | 11/2007 |
| JP | 2010-82188 A | 4/2010 |
| JP | 2013-226619 A | 11/2013 |
| JP | 2014-10546 A | 1/2014 |

* cited by examiner

CONTROL APPARATUS, CONTROL METHOD, AND MEDICAL SUPPORT ARM APPARATUS

TECHNICAL FIELD

The present disclosure relates to a control apparatus, a control method, and a medical support arm apparatus.

BACKGROUND ART

Recently, in the medical field, support arm apparatus are being used to support surgeries. For example, a method is proposed in which an observation unit such as a camera for observing an operative site is provided on the front end of an arm section of a support arm apparatus, and the surgeon performs surgery while viewing an image taken by the observation unit. Alternatively, there is also proposed a method of causing a support arm apparatus to perform work that has been done manually in the past, such as by providing a treatment tool such as forceps on a front end of an arm section, and using the treatment tool.

Herein, some support arm apparatus are provided with a motor and a brake in each joint section, and are configured to drive the arm section with the motor. Additionally, when locking the position and the attitude of the arm section, some support arm apparatus are configured to cause the brake to engage while also cutting off the supply of power to the motor. In such a support arm apparatus, when switching from a state in which the position and the attitude of the arm section are locked by the brake to a state in which the brake is released and the arm section is drivable by the motor, there is concern that the arm section could move due to its own weight.

To prevent this, for example, Patent Literature 1 discloses a technology in which, when releasing a brake and resuming a supply of power to a motor, a compensation amount for compensating the falling of the arm section is added to or subtracted from a command value of the current.

CITATION LIST

Patent Literature

Patent Literature 1: JP H5-138583A

DISCLOSURE OF INVENTION

Technical Problem

Herein, with the technology described in Patent Literature 1, a parameter such as a falling amount corresponding to the configuration of the arm section and the attitude of the arm section is computed in advance, and the above compensation amount is calculated on the basis of the parameter. Consequently in a case in which the surrounding environment changes, such as a case in which the temperature changes, for example, effectively suppressing the falling of the arm section is thought to be difficult.

In light of the above circumstances, in an arm section, when switching between a state in which the position and the attitude are locked by a brake, and a state in Which the arm section is drivable by a motor, there is demand for technology capable of further suppression of the movement of the arm section. Particularly, in a medical support arm apparatus, even tiny movements of the arm section can possibly affect a medical procedure. Consequently, from the perspective of safety, further suppression of the movement of the arm section when switching states is important.

Accordingly, the present disclosure proposes a new and improved control apparatus, control method, and medical support arm apparatus capable of further suppression of the movement amount of an arm section when switching states.

Solution to Problem

According to the present disclosure, there is provided a control apparatus configured to execute a current tracking control on a basis of a measurement value of a torque sensor of an actuator provided in at least one of multiple joint sections included in an arm section of a medical support arm apparatus, the current tracking control causing a motor of the actuator to output torque by which a position and an attitude of the arm section are maintained, and switch a first state in which the motor is driven in accordance with a predetermined control method, and a second state in which the joint section is locked using a brake of the actuator.

In addition, according to the present disclosure, there is provided a control method including: executing a current tracking control on a basis of a measurement value of a torque sensor of an actuator provided in at least one of multiple joint sections included in an arm section of a medical support arm apparatus, the current tracking control causing a motor of the actuator to output torque by which a position and an attitude of the arm section are maintained; and switching a first state in which the motor is driven in accordance with a predetermined control method, and a second state in which the joint section is locked using a brake of the actuator.

In addition, according to the present disclosure, there is provided a medical support arm apparatus including: an arm section provided a medical tool on a front end; and a control apparatus configured to control an operation of the arm section. The control apparatus is configured to execute a current tracking control on a basis of a measurement value of a torque sensor of an actuator provided in at least one of multiple joint sections included in the arm section, the current tracking control causing a motor of the actuator to output torque by which a position and an attitude of the arm section are maintained, and switch a first state in which the motor is driven in accordance with a predetermined control method, and a second state in which the joint section is locked using a brake of the actuator.

According to the present disclosure, in a joint section of an arm section, when switching between a state in which the joint section is driven by a motor in accordance with a regular control method, and a state in which the joint section is locked by a brake, the states are switched after conducting a current tracking control. Also, in the current tracking control, the driving of the motor is controlled such that the position and the attitude of the arm section may be maintained when the states are switched. Consequently, in the instant when the states are switched, the position and the attitude of the arm section are maintained by the current tracking control. Thus, changes in the position and the attitude of the arm section attendant on the switching of states can be suppressed.

Advantageous Effects of Invention

According to the present disclosure as described above, further suppression of the movement amount of an arm section when switching states becomes possible. Note that the effects described above are not necessarily limited, and along with or instead of the effects, any effect that is desired to be introduced in the present specification or other effects that can be expected from the present specification may be exhibited.

MODE(S) FOR CARRYING OUT THE INVENTION

Figure 1:
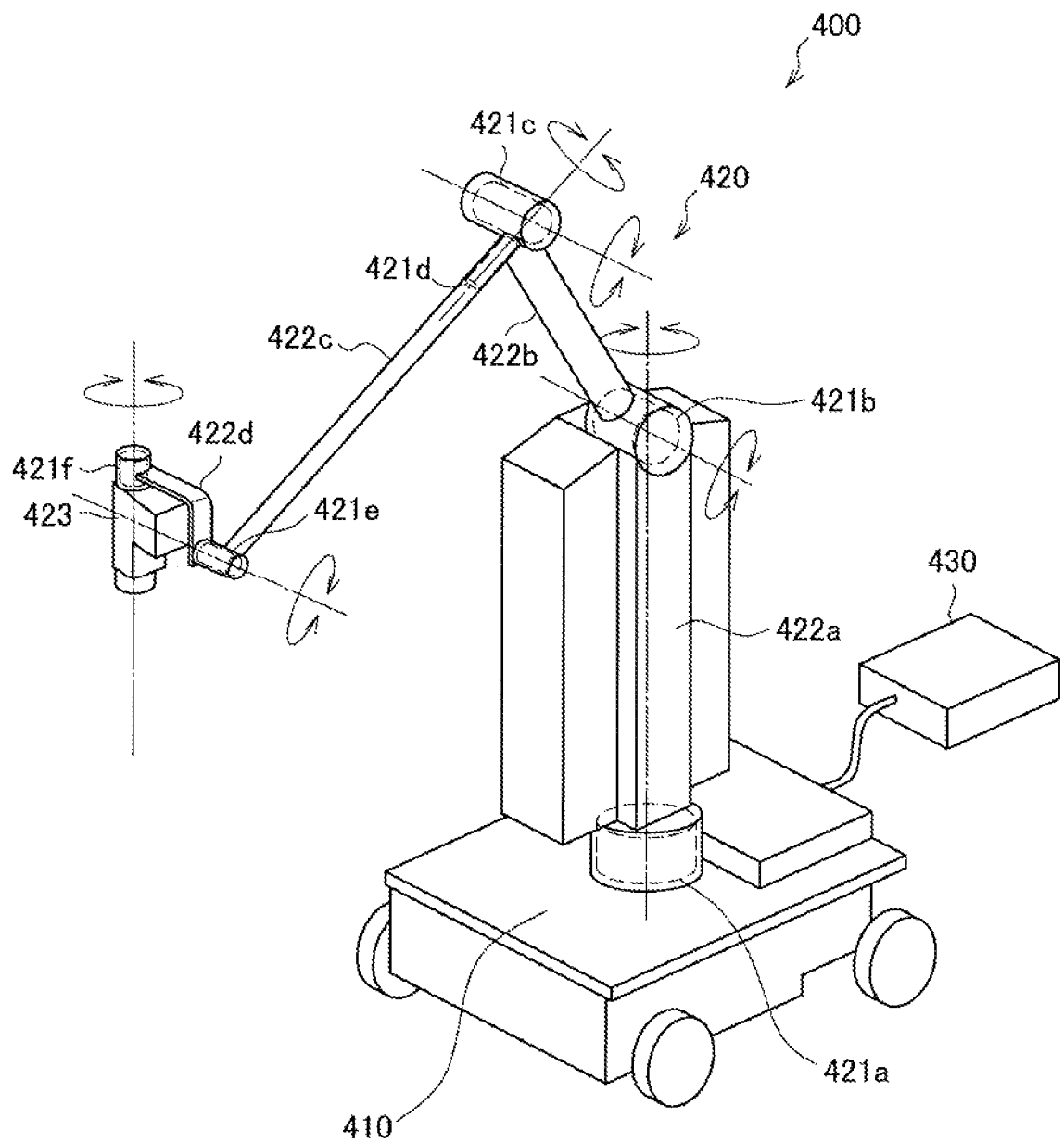
FIG. 1 is a diagram illustrating an overall configuration of a support arm apparatus according to a first embodiment.

Hereinafter, (a) preferred embodiment(s) of the present disclosure will be described in detail with reference to the appended drawings. Note that, in this specification and the drawings, elements that have substantially the same function and structure are denoted with the same reference signs, and repeated explanation is omitted.

Hereinafter, the description will proceed in the following order.
  1. Investigation of medical support arm apparatus
  2. First embodiment
    2-1. Configuration of support arm apparatus
      2-1-1. Overall configuration
      2-1-2. Configuration of actuator
    2-2. System configuration of support arm apparatus
    2-3. Control method
      2-3-1. Brake release control
      2-3-2. Brake engagement control
    2-4. Functional configuration of motor controller
  3. Second embodiment
    3-1. Control method
      3-1-1. Brake release control
      3-1-2. Brake engagement control
    3-2. Functional configuration of motor controller
  4. Modifications
  5. Experiment results
  6. Supplement (1. Investigation of Medical Support Arm Apparatus)

A medical support arm apparatus supports an observation unit or a treatment tool on the front end of an arm section, and is used to provide assistance with medical procedures such as surgeries and examinations performed by a surgeon. For example, with a medical support arm apparatus, there are anticipated uses such as enlarged observation of a tiny region of an operative site by an observation unit such as an imaging unit (also called an electronic imaging microscope), and grasping a patients organ or the like by a treatment tool such as forceps.

Herein, in some medical support arm apparatus, a motor and a brake are provided in each joint section, and the operation of the arm section is controlled by the motor and the brake. For example, in a case of wanting to move an observation unit or a treatment tool to a desired position, and locking the observation unit or the treatment tool at the position, the brake is engaged while a supply of current to the motor is also stopped, and the position and the attitude of the arm section are locked. In the following description, such a state in which each joint section is locked by the brake (that is, a state in which the position and the attitude of the arm section are locked) is also called the locked state.

In the locked state, in a case in which a need to change the position of the observation unit or treatment tool is produced, the brake is released while current is also supplied to the motor, the motor is driven in accordance with regular control (for example, position control or force control), and the arm section operates in accordance with the regular control. In the following description, such a state in Which the driving of each joint section is controlled in accordance with a predetermined control method during regular operation (that is, a state in which the position and the attitude of the arm section are able to operate in accordance with a predetermined control method during regular operation) is also called the regular operating state.

Herein, particularly in a medical support arm apparatus, the movement amount of the arm section when switching between the locked state and the regular operating state is demanded to be extremely small. This is because if the arm section moves, and the position of the observation unit or the treatment tool changes, it becomes necessary to correct the position of the observation unit or the treatment tool, thereby impeding the smooth execution of a medical procedure. Particularly, in a case of performing enlarged observation of a tiny site with an observation unit, even slight movements of the observation unit cause the field of view to change greatly; and thus it is desirable to keep the movement amount of the observation unit as small as possible.

Also, a medical support arm apparatus is demanded to be compact, so as not to be an obstacle to the surgeon. For example, with a medical support arm apparatus, there is anticipated a usage scenario in which an image of an operative site taken by the observation unit is projected onto a display apparatus inside the operating room, and the surgeon performs surgery while watching the image. In this case, if the configuration of the arm section is large, there is a risk that the field of view of the surgeon watching the display apparatus may be blocked, or that the arm section may hinder the surgeon's work on the operative site.

To configure the arm section more compactly, further miniaturization of the motor provided in each joint section is also demanded. Consequently, since the motor needs to have a predetermined driving force while also being compact, there is a tendency to generate more heat as compared to a large-sized motor. Thus, to inhibit the generation of heat, proactive utilization of the brake when stationary is anticipated. In this way, in a medical support arm apparatus, a high frequency of switching between the locked state and the regular operating state is anticipated, and thus keeping the movement amount of the arm section small when switching is more important.

Accordingly, the inventors thoroughly investigated technology capable of further suppression of the movement of the arm section when switching between the locked state and the regular operating state. The following describes a preferred embodiment of the present disclosure conceived by the inventors as a result of the investigation. Note that, in light of the above circumstances, the technology that may be provided in the present disclosure can be said to exhibit a large effect particularly in a medical support arm apparatus. Accordingly, as one example, the following will describe an embodiment in which technology according to the present disclosure is applied to a medical support arm apparatus. However, the present disclosure is not limited to such an example, and the present disclosure may also target an industrial support arm apparatus used for product assembly, product inspection, or the like in a factory, for example.

(2. First Embodiment)
(2-1-1. Configuration of Support Arm Apparatus)
(2-1-1. Overall Configuration)

An overall configuration of a support arm apparatus according to a first embodiment of the present disclosure will be described with reference to FIG. 1. FIG. 1 is a diagram illustrating an overall configuration of a support arm apparatus according to the first embodiment.

Referring to FIG. 1, a support arm apparatus 400 is equipped with a base section 410, an arm section 420, and a control apparatus 430. The support arm apparatus 400 is a medical support arm apparatus that may be applied favorably to surgeries, examinations, and the like.

The base section 410 is a base for the support arm apparatus 400, and the arm section 420 is extended from the base section 410. The base section 410 is provided with casters, and the support arm apparatus 400 is grounded on the floor face via the casters and configured to be movable on the floor face with the casters. However, the configuration of the support arm apparatus 400 according to the first embodiment is not limited to such an example. For example, the support arm apparatus 400 may be configured in which the base section 410 is not provided, and the arm section 420 is attached directly to the ceiling or a wall of the operating room. For example, in the case in which the arm section 420 is attached to the ceiling, the support arm apparatus 400 is configured so that the arm section 420 hangs down from the ceiling.

The arm section 420 includes multiple joint sections 421a to 421f, multiple links 422a to 422d that are connected with one another by the joint sections 421a to 421e, and an imaging unit 423 installed at the front end of the arm section 420.

The links 422a to 422d are rod-like members. One end of the link 422a is connected with the base section 410 through the joint section 421a, the other end of the link 422a is connected with one end of the link 422b through the joint section 421b, and the other end of the link 422b is further connected with one end of the link 422c through the joint sections 421c and 421d. Furthermore, the other end of the link 422c is connected with one end of the approximately L-shaped link 422d through the joint section 421e, while the other end of the link 422d and the imaging unit 423 are connected through the 421f. As described above, the arm shape extending from the base section 410 is configured such that the base section 410 serves as a support point, and the ends of the multiple links 422a to 422d and the imaging unit 423 are connected with one another through the joint sections 421a to 421f.

The imaging unit 423 is an example of an observation unit for observing an operative site, and is a camera or the like capable of taking a moving image and/or a still image of an imaging target, for example. An image of the patient's operative site taken by the imaging unit 423 is displayed on a display apparatus (not illustrated) provided in the operating room, for example, and the surgeon performs surgery while observing the image of the patient's operative site displayed on the display apparatus. In this way, the support arm apparatus 400 may be the observation apparatus 400 in which an observation unit is attached to the front end of the arm section 420. As the observation unit, other apparatus may be provided, such as an endoscope, or an optical microscope by which the surgeon performs enlarged observation of the operative site directly through an eyepiece, for example. Note that among types of observation apparatus 400, the support arm apparatus 400 in which the imaging unit 423 is provided on the front end of the arm section 420 is also called a video microscope apparatus 400.

However, the front end unit provided on the front end of the arm section 420 is not limited to an observation unit, and any of various types of medical tools may be attached to the front end of the arm section 420 as the front end unit. For example, any of various types of treatment tools, such as forceps or a retractor, may be connected as the front end unit. Alternatively, a light source for an endoscope or a microscope, or a surgical energy device used to seal blood vessels, for example, may be connected as the front end unit.

The joint sections 421a to 421f are provided with actuators 300 illustrated in FIG. 2 to be described later, and the joint sections 421a to 421f are configured to be rotatable about predetermined rotating shafts according to the driving of motors 310 of the actuators 300. The driving of the motors 310 is controlled by the control apparatus 430. By controlling the driving of the motor 310 in each of the joint sections 421a to 421f, driving of the arm section 420 is controlled so as to extend or contract (fold up) the arm section 420, for example.

Also, a brake that restrains the rotating shaft of the joint sections 421a to 421f is provided in the actuator 300. Additionally, by control from the control apparatus 430, the state of each joint section is switched between a locked state and a regular operating state. In the following description, a control that switches the locked state to the regular operating state is also called the brake release control, while a control that switches the regular operating state to the locked state is also called the brake engagement control. Details about the brake release control and the brake engagement control will be described fully in (2-3. Control method) below.

Note that, in the illustrated example, the support arm apparatus 400 includes six joint sections 421a to 421f, and six degrees of freedom are realized with respect to the driving of the area section 420. By configuring the arm section 420 to have six degrees of freedom, the imaging unit 423 can be moved freely within the movable range of the arm section 420. Consequently, it becomes possible to use the imaging unit 423 to image the operative site from a variety of angles and distances. However, the configuration of the arm section 420 is not limited to the illustrated example, and the numbers of the joint sections 421a to 421f and the links 422a to 422c, their arrangement, the directions of the drive shafts of the joint sections 421a to 421f, and the like may be set appropriately so that the arm section 420 has the desired degrees of freedom. However in consideration of freedom in the position and the attitude of the imaging unit 423, the arm section 420 favorably may be configured to have six or more degrees of freedom.

The control apparatus 430 includes a processor, such as a central processing unit (CPU) or a digital signal processor (DSP), for example, or a microcontroller, a control board or the like with these processors installed onboard. By executing signal processing according to a predetermined program, the control apparatus 430 controls the operation of the support arm apparatus 400.

The method of controlling the support arm apparatus 400 is not particularly limited, and the operation of the support arm apparatus 400 may be controlled by the control apparatus 430 by any of various brown control methods, such as position control or force control. In the case of controlling the support arm apparatus 400 by position control, an input apparatus such as a controller for operating the arm section 420 may be provided. In the case of controlling the support arm apparatus 400 by force control, the operation of the arm section 420 may be controlled so that the arm section 420 moves in the direction of the force applied to the arm section 420 in response to an operation attempting to move the arm section 420 which is performed by a user touching the arm section 420 directly, for example. Note that, since any of various brown methods may be used as the specific methods of controlling the support arm apparatus 400 by position control or force control, a detailed description is omitted herein.

In addition, the control apparatus 430 switches the locked state and the regular operating state by appropriately controlling the operation of the actuator 300 in the joint sections 421a. to 421f of the arm section 420. Details about the control during switching will be described fully in (2-2. System configuration of support arm apparatus) below and in (2-3. Control method) below.

Note that, in the illustrated example, the control apparatus 430 is connected to the base section 410 through a cable, but by providing a control board or the like having functions similar to those of the control apparatus 430 internally inside the base section 410 the base section 410 and the control apparatus 430 may be configured in an integrated manner. Alternatively, the functions of the control apparatus 430 may be distributed among multiple control boards or the like, and these multiple control boards or the like may be disposed in the base section 410 and the arm section 420 in a distributed manner. For example, a control board (corresponding to a motor controller 200 described later) or the like for controlling the driving of the actuator 300 in each of the joint sections 421a to 421f may be provided near each of the joint sections 421a to 421f.

The above thus describes a schematic configuration of the support arm apparatus 400 according to the first embodiment with reference to FIG. 1.

(2-1-2. Configuration of Actuator)

A configuration of the actuator 300 provided in each of the joint sections 421a to 421f of the support arm apparatus 400 illustrated in FIG. 1 will be described with reference to FIG. 2. FIG. 2 is an exploded perspective view illustrating an exemplary configuration of the actuator 300 provided in each of the joint sections 421a to 421f of the support arm apparatus 400 according to the first embodiment.

Figure 2:
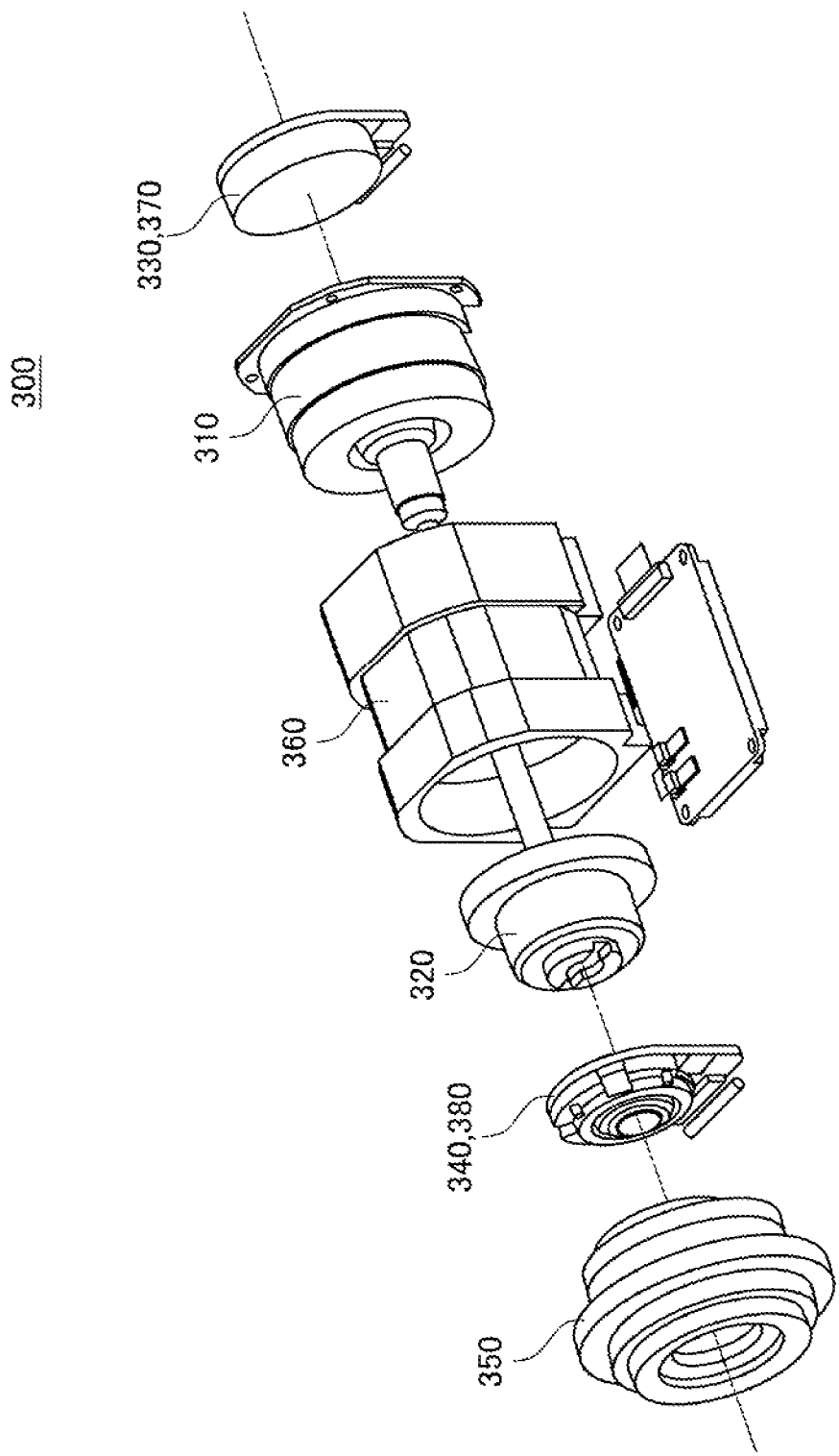
FIG. 2 is an exploded perspective view illustrating an exemplary configuration of an actuator provided in each joint section of the support arm apparatus according to the first embodiment.

Referring to FIG. 2, the actuator 300 is provided with a motor 310, a speed reducer 320, an input shaft encoder 330, an output shaft encoder 340, an output shaft 350, a housing 360, a brake 370, and a torque sensor 380. In the actuator 300, the rotation of the rotating shaft of the motor 310 is reduced by the speed reducer 320 at a predetermined reduction ratio, and transmitted to other downstream members through the output shaft 350. As a result, the other members are driven.

The housing 360 has an approximately cylindrical shape, in which the respective component members are housed internally. In a state in which each of the component members is housed inside the housing 360, the actuator 300 is installed into each of the joint sections 421a to 421f of the support arm apparatus 400 described above.

The motor 310 is a driving mechanism that, in a case of being given a predetermined command value (current value), causes a rotating shaft to rotate at torque corresponding to the command value, thereby producing driving force. As the motor 310, a brushless motor is used, for example. However, the first embodiment is not limited to such an example, and any of various known types may be used as the motor 310.

The speed reducer 320 is joined to the rotating shaft of the motor 310. The speed reducer 320 reduces the rotational velocity of the rotating shaft of the joined motor 310 (in other words, the rotational velocity of the input shaft) at a predetermined reduction ratio, and transmits to the output shaft 350. In the first embodiment, the configuration of the speed reducer 320 is not limited to a specific configuration, and any of various brown types may be used as the speed reducer 320. However, as the speed reducer 320, it is favorable to use one capable of setting a relatively large reduction ratio, such as a Harmonic Drive (registered trademark), for example. In addition, the reduction ratio of the speed reducer 320 may be set appropriately according to the application of the actuator 300. For example, in the case of applying the actuator 300 to the joint sections 421a to 421f of the support arm apparatus 400 as in the first embodiment, the speed reducer 320 having a reduction ratio of approximately 1:100 may be used favorably.

The input shaft encoder 330 detects the rotational angle of the input shaft (that is, the rotational angle of the motor 310). The output shaft encoder 340 detects the rotational angle of the output shaft 350. The configuration of the input shaft encoder 330 and the output shaft encoder 340 is not limited, and any of various known types of rotary encoders, such as magnetic encoders or optical encoders, for example, may be used as the input shaft encoder 330 and the output shaft encoder 340.

The brake 370 has a function of restraining the rotating shaft of the actuator 300, and stopping the rotation of the actuator 300. In the illustrated example, the brake 370 is configured in an integrated manner with the input shaft encoder 330, and is configured to stop the rotation of the actuator 300 by restraining the rotating shaft of the motor 310 (that is, the input shaft). Note that the specific configuration of the brake 370 is not limited, and any of various known types of brakes, such as an electromagnetic brake, for example, may be used as the brake 370.

Note that in the actuator 300, since the speed reducer 320 is provided between the input shaft and the output shaft 350, the torque of the output shaft 350 becomes greater relatively. Consequently, in the hypothetical case of providing the brake 370 on the output shaft 350, a larger braking force is required of the brake 370. Thus, there is a possibility that the brake 370 may be bulkier. In the first embodiment, by providing the brake 370 on the input shaft as illustrated in the drawing, the actuator 300, that is, the joint sections 421a to 421f, can be miniaturized further.

The torque sensor 380 measures the torque produced in the output shaft 350. The torque sensor 380 is able to detect both the torque (generated torque) output by the motor 310, and the torque (external torque) imparted from the outside. In the illustrated example, the torque sensor 380 is configured in an integrated manner with the output shaft encoder 340. Note that the specific configuration of the torque sensor 380 is not limited, and any of various known types of force sensors, such as a strain sensor, for example, may be used as the torque sensor 380.

Note that the arrangement of the brake 370 and the torque sensor 380 is not limited to the illustrated example. The brake 370 may also be arranged as a member different from the input shaft encoder 330. Additionally, the torque sensor 380 may also be arranged as a member different from the output shaft encoder 340.

The above describes a configuration of the actuator 300 according to the first embodiment with reference to FIG. 2. Note that the actuator 300 additionally may be provided with other components besides the illustrated components. For example the actuator 300 additionally may be provided with any at various types of members that may be included in a typical actuator, such as a driver circuit (driver integrated circuit (IC)) that induces rotational driving in the motor 310 by supplying a current to the motor 310.

Herein, as described above, the actuator 300 is an actuator with a built-in brake, in which the brake 370 is attached directly to the drive shaft (input shaft) of the motor 310.

Generally, in the control during regular operation, such as position control or force control, a control quantity necessary to realize a desired position and attitude is computed by sensing the position and the attitude of the arm section 420 on the basis of measurement values of the rotational angle and the torque of the actuator 300 in each of the joint sections 421a to 421f. On the other hand, as above, in the actuator 300, the rotation of the drive shaft of the motor 310 is stopped directly by the brake 370. Consequently, attempting to conduct control dining regular operation while still in the locked state results in a state in which the measurement value of the input shaft encoder 330 or the output shaft encoder 340 does not change even through the motor 310 is driving, thus producing a malfunction in the control.

Therefore, with an actuator with a built-in brake like the actuator 300, switching between the locked state and the regular operating state requires that the control during regular operation be started after releasing the brake, so that these two states do not overlap in time. However, in the case of simply conducting such a switching control, an exclusive time occurs in which the brake is not engaged and the control during regular operation is also not started, and a situation may occur in which the arm section moves greatly due to its own weight.

Accordingly, in the first embodiment, in the control that switches the locked state to the regular operating state (hereinafter also called the brake release control) and in the control that switches the regular operating state to the locked state (hereinafter also called the brake engagement control), control is conducted to keep the movement amount of the arm section 420 even smaller. Hereinafter, the brake release control and the brake engagement control according to the first embodiment will be described in detail.

(2-2. System Configuration of Support Arm Apparatus)

Figure 3:
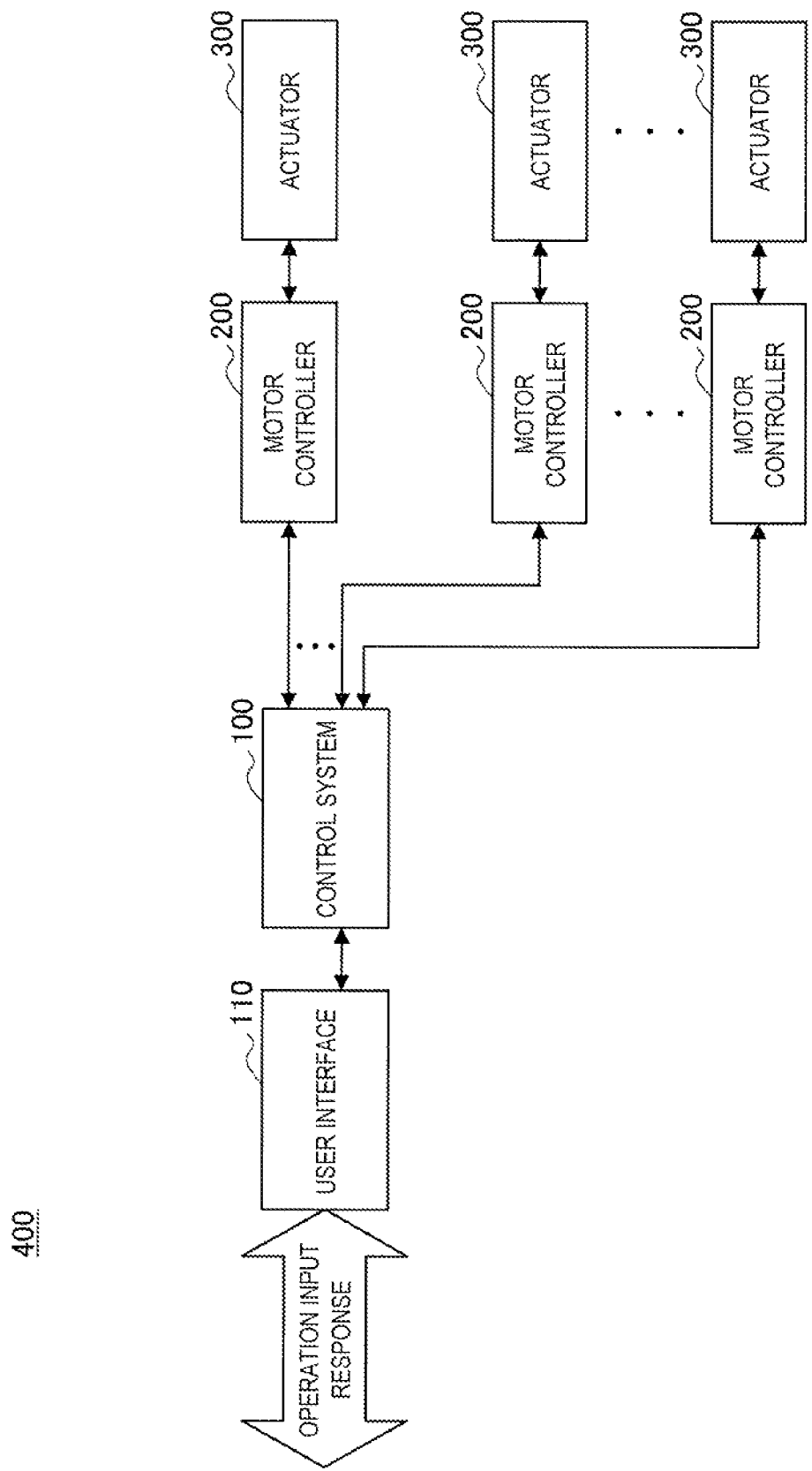
FIG. 3 is a bib& diagram illustrating a system configuration of the support arm apparatus according to the first embodiment.

A system configuration of a support arm apparatus according to the first embodiment will be described with reference to FIG. 3. FIG. 3 is a block diagram illustrating, a system configuration of a support arm apparatus according to the first embodiment. Note that FIG. 3 illustrates the system of the support arm apparatus 400 described with reference to FIG. 1 in a simulated manner as blocks and connections between the blocks.

Note that, in FIG. 3, to describe the brake release control and the brake release control according to the first embodiment, only the components necessary for these controls are illustrated primarily, while the other components are omitted from illustration. However, the support arm apparatus 400 may include components for realizing various types of operations which are executable by a typical existing support arm apparatus, such as components for causing the arm section 420 to operate by position control or force control, for example.

Referring to FIG. 3. the support arm apparatus 400 primarily includes a control system 100, the actuator 300 provided in each of the joint sections 421a to 421f of the arm section 420, and a motor controller 200 which is provided with respect to each actuator 300, and controls the operation of each actuator 300. Note that the actuator 300 corresponds to the actuator 300 described with reference to FIG. 2.

The motor controller 200, in accordance with control from the control system 100, controls the driving of the motor 310 and the brake 370 of the actuator 300 assigned to itself. Specifically, the motor controller 200, in accordance with control from the control system 100, executes the brake release control (that is, releases the brake 370 while also driving the motor 310 in accordance with the control during regular operation). In addition, the motor controller 200, in accordance with control from the control system 100, executes the brake engagement control (that is, engages the brake 370 to lock each of the joint sections 421a to 421f while also stopping the supply of current to the motor 310).

Additionally, during regular operation, the motor controller 200, in accordance with control from the control system 100, controls the driving of the motor 310 so that each of the joint sections 421a to 421f rotates by an amount corresponding to a control quantity computed in accordance with a predetermined method of position control or force control. Note that since any of various known methods may be used as the specific methods of position control or force control, a detailed description is omitted herein.

Note that, as an actual apparatus configuration, the multiple motor controllers 200 may be different configurations, or the functions thereof may be aggregated all together in a single configuration (such as a control board or the like, for example). For example, a control board or the like having functions corresponding to the single motor controller 200 may be provided in each of the joint sections 421a to 421f, or the functions of the multiple motor controllers 200 may be aggregated inside the control apparatus 430 illustrated in FIG. 1.

The control system 100 centrally controls the operation of the arm section 420 by controlling the operations of the multiple motor controllers 200 in a coordinated manner. Specifically, the control system 100, by appropriately controlling the operations of each motor controller 200, causes each motor controller 200 to execute the brake release control and the brake engagement control. Also, during regular operation, the control system 100 computes a control quantity with respect to the motor 310 in each of the joint sections 421a to 421f in accordance with any of various known types of methods of position control or force control, and causes each motor controller 200 to drive the motor 310 in accordance with the control quantity. Note that the functions of the control system 100 may be realized by the control apparatus 430 illustrated in FIG. 1, for example.

The operations of the arm section 420 in accordance with the brake release control, the brake engagement control, and the control during regular operation in the control system 100 may be conducted in accordance with operation input by a user through a user interface 110. Operation input by the user may be conducted through an input device such as a lever or switch, for example, or may be conducted by a direct operation with respect to the arm section 420, like moving the arm section 420 directly by hand. Specifically, for example, the switching of these controls may be conducted explicitly by an operation with respect to a switch or the like. Alternatively, for example, the control system 100 may execute the brake release control in the case in which the user attempts to move the arm section 420 directly by hand, and the control system 100 may execute the brake engagement control in the case in which the user removes one's hand from the arm section 420.

(2-3. Control Method)

Details about the brake release control and the brake engagement control according to the first embodiment executed in the system configuration illustrated in FIG. 3 will be described. Note that each of the processes illustrated in FIGS. 4 and 5 described below corresponds to a process executed with respect to each corresponding actuator in each of the motor controllers 200 illustrated in FIG. 3.

(2-3-1. Brake Release Control)

Figure 4:
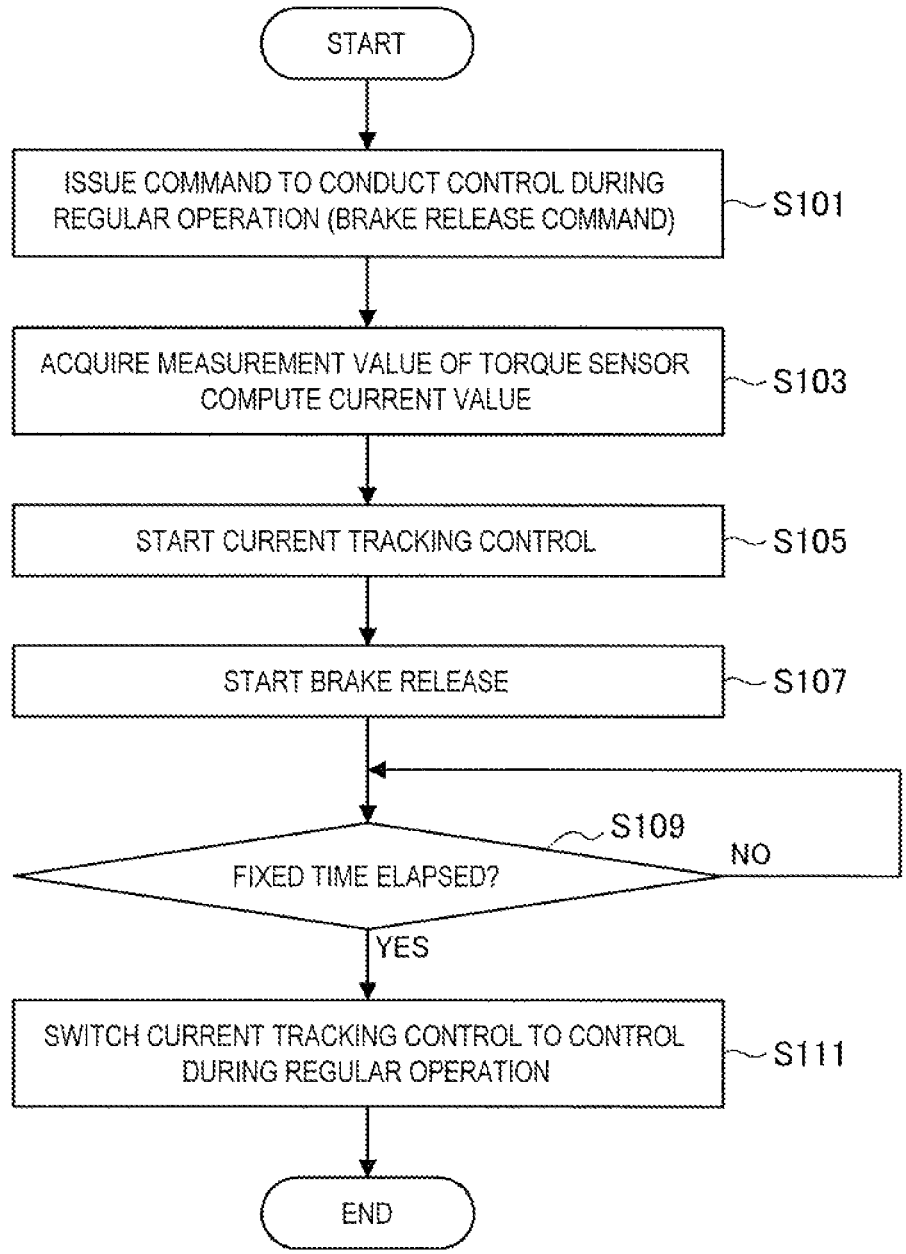
FIG. 4 is a flowchart illustrating an example of a processing procedure of a brake release control according to the first embodiment.

A processing procedure of the brake release control according to the first embodiment will be described with reference to FIG. 4. FIG. 4 is a flowchart illustrating an example of a processing procedure of the brake release control according to the first embodiment.

Referring to FIG. 4, in the brake release control according to the first embodiment, first, a command to conduct the control during regular operation in the actuator 300, or in other words, a command to release the brake 370, is input (step S101). In the case in which the position and the attitude of the arm section 420 are locked by the brake 370, the command may be issued from the control system 100 to each motor controller 200 in response to an operation of the user attempting to move the arm section 420.

Next, a measurement value of the torque sensor 380 is acquired, and a current value for driving the motor 310 is computed on the basis of the measurement value (step S103). Specifically, in step S103, first, in the state in which the position and the attitude of the arm section 420 are locked by the brake 370, the measurement value of the torque sensor 380 is used to compute a necessary torque value that the motor 310 should output for the state to be realized by the motor 310 of the actuator 300 (that is, a torque value that the motor 310 should output so that, even in the case in which the brake 370 is released, the position and the attitude of the arm section 420 may still be maintained by the motor 310). Subsequently, a current value necessary to output the computed torque value is computed from a torque constant of the motor 310.

Subsequently, the motor 310 is driven in accordance with the computed current value (step S105). Hereinafter, such a control of driving the motor 310 by a current value tracking a measurement value of a torque sensor so that the position and the attitude of the arm section 420 are maintained will be called the current tracking control for the sake of convenience, in order to distinguish from the regular position control or force control.

After the current tracking control is conducted, next, the release of the brake 370 is started (step S107). In this way, in the first embodiment, the release of the brake 370 is started in a state in Which the current tracking control is being executed.

Next, it is determined whether or not a fixed time has elapsed (step S109). Only in the case in which the fixed time has elapsed, the flow proceeds to step S111, and the switching from the current tracking control to the control during regular operation (that is, position control or force control) is conducted. In other words, the switching from the current tracking control to the control during regular operation is conducted ager standing by until a fixed time elapses from the start of the release of the brake 370.

The fixed time may be a time from the start of the release of the brake 370 until the brake 370 is actually released. In other words, the process in step S109 is a process of standing by until the release of the brake 370 functions effectively. This is because generally, in the brake 370, during the period from the start of release until the mechanical mechanism that is restraining the rotating shaft actually releases the restraint completely a predetermined time lag is produced, such as the time during which the mechanism moves physically. The time is defined as a specification in accordance with the type of the brake 370, for example. Consequently, the specific value of the fixed time in step S109 may be set appropriately in accordance with the specifications of the brake 370. For example, the fixed time may be approximately from several dozen to several hundred milliseconds.

The above describes a processing procedure of the brake release control according to the first embodiment with reference to FIG. 4. As described above, according to the first embodiment, when transitioning from the locked state to the regular operating state, the brake 370 is released after the current tracking control is conducted. Herein, in the current tracking control, the load acting on each actuator 300 after the release of the brake 370 is predicted on the basis of the measurement value of the torque sensor 380, and the motor 310 is driven by a current value by which a torque corresponding to the load is output. Consequently according to the first embodiment, in the instant when the brake 370 is released, even though the control during regular operation is not being conducted yet, the position and the attitude of the arm section 420 may be maintained by the current tracking control, and thus the movement amount of the imaging unit 423 is suppressed further. Thus, smooth execution of medical procedures is realized, without the surgeon's work being impeded.

Herein, as another method of control when transitioning from the locked state to the regular operating state, a method of beginning to start the control during regular operation in a dead time from beginning to release the brake until the brake is actually released is conceivable. However, with this method, to ensure a margin while accounting for variations. an exclusive time occurs in which the brake is not engaged and the control during regular operation is also not functioning normally, and there is a risk of the position and the attitude of the inn section changing greatly. According to the first embodiment, by beginning to release the brake 370 after conducting the current tracking control as above, the occurrence of such an exclusive time can be prevented.

Also, in the first embodiment, the current tracking control may be conducted dynamically on the basis of the measurement value of the torque sensor. Herein, with existing technology as exemplified by Patent Literature 1, a compensation amount of the change in the position and the attitude of the arm section is computed on the basis of a parameter which is a fixed value. However, due to differences in. the attitude of the arm section 420 and the external environment, such as the ambient temperature, the torque acting on each joint section (actuator 300) is different. Consequently, with such existing technology, there is a possibility of being unable to effectively suppress changes in the position and the attitude of the arm section. On the other hand, in the first embodiment, since the current trading control is conducted dynamically on the basis of the measurement value of the torque sensor as above, the torque that the motor 310 should output at the time is computed dynamically in accordance with the attitude of the arm section 420 and the external environment, and changes in the position and the attitude of the arm section 420 can be suppressed with higher accuracy.

Also, generally, in the case of controlling a certain physical quantity to match a predetermined target value, in the case of a large difference between the target value and the current value, the overshoot in the response and the time until convergence become greater (that is, the transient response worsens). For example, like the example described above, in the case in which the control during regular operation is started after releasing the brake, the generated torque of the motor when the control during regular operation is started is approximately zero, and from this state the motor must be controlled so that the generated torque tracks a predetermined target value. Thus, the transient response is thought to worsen readily.

On the other hand, in the first embodiment, when the control during regular operation is started, the current tracking control is already being conducted. Also, since the current tracking control is being conducted to maintain the position and the attitude of the arm section 420 when the control during regular operation is started, when the current tracking control is switched to the control during regular operation, a value close to the target value of the generated torque when the control during regular operation is started (that is, a target value of the current to apply to the motor 310) is already realized. Consequently, when the control during regular operation is started, the target value does not fluctuate greatly, and worsening of the transient response is restrained. Thus, changes in the position and the attitude of the arm section 420 attendant on the switching of states may be suppressed further.

Note that, in the first embodiment, the respective torque constants of each motor 310 provided in each actuator 300 may be stored in a storage area in each actuator 300. a storage area in each motor controller 200, or the like. In addition, in the current tracking control, a target value of current may be computed for each actuator 300 by using the torque constant corresponding to the motor 310 provided in the actuator 300 itself. Generally, since the torque constant is a unique constant that varies for each motor 310, by using a torque constant corresponding to each motor 310 in this way, the current tracking control can be conducted with higher accuracy. Additionally, the torque constant may also change due to temperature. Consequently, in the first embodiment, a temperature sensor may be provided in the actuator 300, and the current tracking control may also be conducted after correcting the torque constant on the basis of a measurement value of the temperature sensor. Furthermore, it is known that the torque constant may also vary due to the angle of the rotating shaft of the motor 310, the magnitude of the current applied to the motor 310, and the like. Consequently, the current tracking control may also be conducted after correcting the torque constant on the basis of the angle of the rotating shaft detected by the input shaft encoder 330 or the output shaft encoder 340, or the current value currently being applied to the motor 310. By conducting these correction processes, the accuracy of the current tracking control can be improved further.

Note that, as described above, the process in step S109 is a process of standing by until the release of the brake 370 functions effectively. In the example illustrated in FIG. 4, the process is a process of standing by until a fixed time elapses, but the first embodiment is not limited to such an example. In step S109, a process that confirms whether or not the release of the brake 370 is functioning effectively may also be conducted. Subsequently, as a result of the process, in the case of determining that the release of the brake 370 is functioning effectively, the switching from the current tracking control to the control dining regular operation may be conducted.

For example, in step S109, on the basis of a measurement value of the output shaft encoder 340, in the case in which the angle of the output shaft changes a predetermined value or more, it may be determined that the release of the brake 370 is functioning effectively. This is because even in the case in which the current tracking control is being conducted, when the brake 370 is released, the rotational angle of the output shaft is thought to change, even if only slightly (see FIG. 12 described later).

Herein, in the first embodiment, by using a measurement value of the output shaft encoder 340 rather than a measurement value of the input shaft encoder 330, the release of the brake 370 can be determined with higher accuracy. The reason for this is because, as described with reference to FIG. 2, in the actuator 300 according to the first embodiment, the speed reducer 320 and the torque sensor 380 are provided between the motor 310 and the output shaft 350, and thus backlash of the speed reducer 320, strain of the torque sensor 380, and the like may cause a discrepancy to occur in the transmission of the angle between the motor shaft and the output shaft 350. In other words, there is a possibility that the measurement value of the input shaft encoder 330 does not necessarily indicate the rotational angle of the output shaft 350 accurately. Consequently, by using a measurement value of the output shaft encoder 340, the angle change of the output shaft 350 can be ascertained with higher accuracy, and the determination of whether or not the brake 370 has been released according to the angle change can be conducted with higher accuracy.

(2-3-2. Brake Engagement Control)

Figure 5:
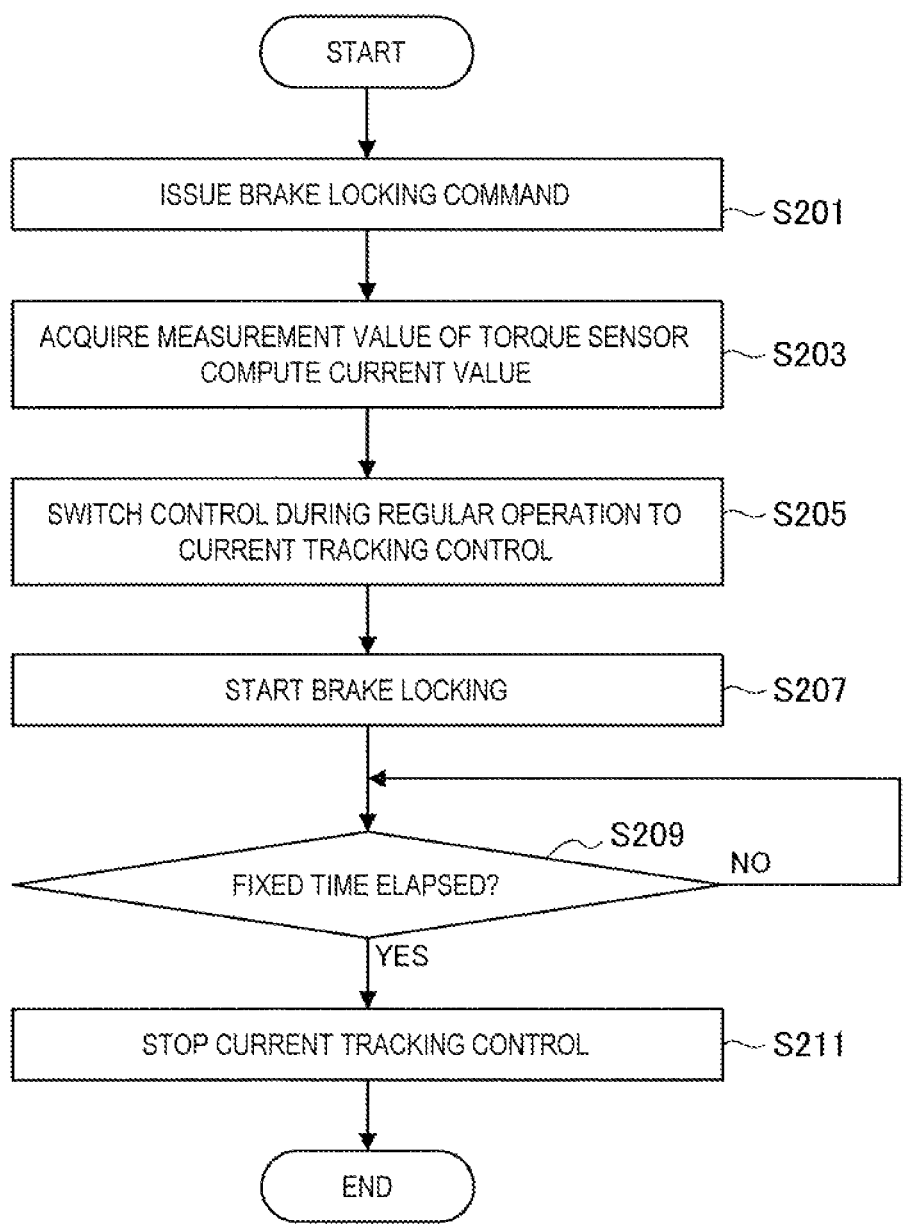
FIG. 5 is a flowchart illustrating an example of a processing procedure of a brake engagement control according to the first embodiment.

A processing procedure of the brake engagement control according to the first embodiment will be described with reference to FIG. 5. FIG. 5 is a flowchart illustrating an example of a processing procedure of the brake engagement control according to the first embodiment.

Referring to FIG. 5, in the brake engagement control according to the first embodiment, first, a brake locking command, that is, a command to stop the control during regular operation in the actuator 300 and lock the joint section with the brake 370, is input (step S201). The command may be issued from the control system 100 to each motor controller 200 in response to an operation of the user attempting to engage the brake 370.

Next, a measurement value of the torque sensor 380 is acquired, and a current value for driving the motor 310 is computed on the basis of the measurement value (step S203). Specifically in step S203, a current value for conducting the current tracking control is computed, similarly to the process in step S103 in the brake release control described above. In other words, the measurement value of the torque sensor 380 is used to compute a necessary torque value that the motor 310 should output for the current state of attempting to lock the position and the attitude of the arm section 420 with the brake 370 to be realized by the motor 310 of the actuator 300 (that is, a torque value that the motor 310 should output so that, even in the state in which the brake 370 is not engaged, the position and the attitude of the arm section 420 may still be maintained by the motor 310). Subsequently a current value necessary to output the computed torque value is computed from a torque constant of the motor 310.

Subsequently, the motor 310 is driven in accordance with the computed current value, that is, the switching from the control during regular operation to the current tracking control is conducted (step S205).

After the current tracking control is conducted, next, the locking of the rotating shaft by the brake 370 is started (step S207). In this way, in the first embodiment, the locking by the brake 370 is started in a state in which the current tracking control is being executed.

Next, it is determined whether or not a fixed time has elapsed (step S209). Only in the case in which the fixed time has elapsed, the flow proceeds to step S211, and the current tracking control is stopped. In other words, the current tracking control is stopped after standing by until a fixed time elapses from the start of the locking of the rotating shaft by the brake 370.

The fixed time may be a time from the start of the locking of the rotating shaft by the brake 370 until the locking of the rotating shaft by the brake 370 actually functions. In other words, the process in step S209 is a process of standing by until the locking by the brake 370 functions effectively. This is because, similar to when releasing the brake generally, in the brake 370, during the period from the start of the locking of the rotating shaft until the mechanical mechanism for restraining the rotating shaft actually completes the restraint entirely, a predetermined time lag occurs, such as the time during which the mechanism moves physically. The time is defined as a specification in accordance with the type of the brake 370, for example. Consequently the specific value of the fixed time in step S209 may be set appropriately in accordance with the specifications of the brake 370. For example, the fixed time may be approximately from several dozen to several hundred milliseconds.

The above describes a processing procedure of the brake engagement control according to the first embodiment with reference to FIG. 5. According to the brake engagement control according to the first embodiment, effects similar to those of the brake release control described above can be obtained. Namely, according to the brake engagement control according to the first embodiment, when transitioning from the regular operating state to the locked state, the rotating shaft is locked by the brake 370 after switching from the control during regular operation to the current tracking control. Consequently, in the instant when the rotating shaft is locked by the brake 370, even though the control during regular operation is not being conducted, the position and the attitude of the arm section 420 are maintained by the current tracking control, and thus the movement amount of the imaging unit 423 is suppressed further. Thus, smooth execution of medical procedures is realized, without the surgeon's work being impeded. Also, at this time, since the current tracking control is conducted dynamically on the basis of a measurement value of a torque sensor, dynamic current tracking control corresponding to changes in the attitude of the arm section 420 and changes in the external environment can be conducted, and changes in the position and the attitude of the arm section 420 can be suppressed further.

Note that, in the brake engagement control, similarly to the brake release control, the current tracking control may be conducted using a unique torque constant for each motor 310. At this time, a temperature con with respect to the torque constant may also be conducted in addition.

Additionally, the process in step S209 may be another process insofar as the process is capable of determining that the locking of the rotating shaft by the brake 370 is functioning effectively. At this time, by using a measurement value of the output shaft encoder 340 for the determination, a more accurate determination process, from which the influence of backlash of the speed reducer 320, strain of the torque sensor 380, and the like has been eliminated, can be conducted.

(2-4. Functional Configuration of Motor Controller)

Figure 6:
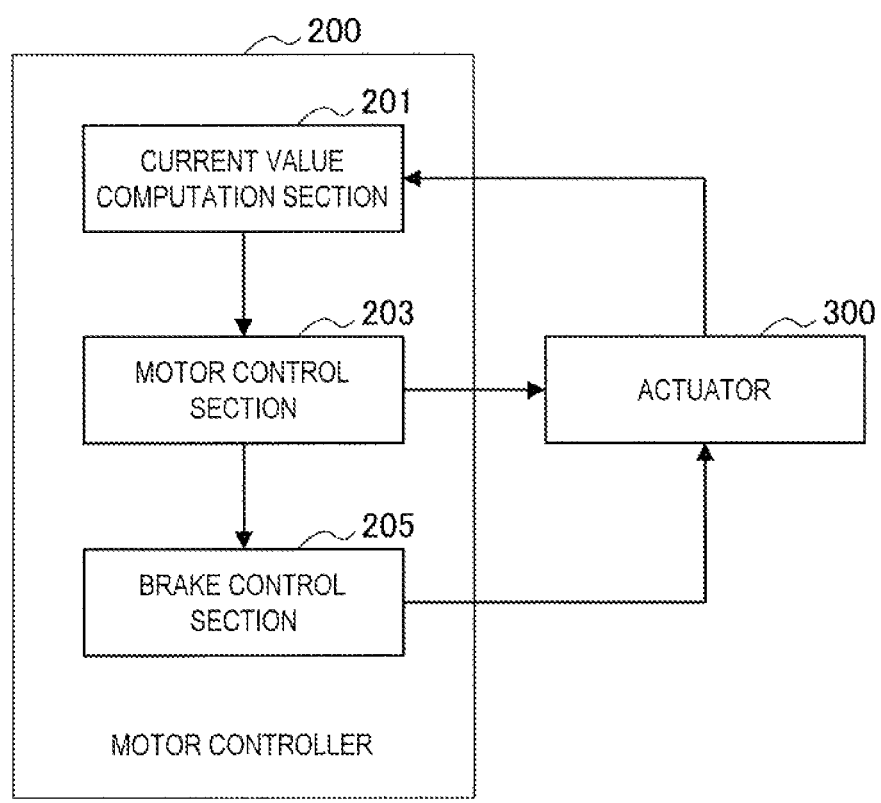
FIG. 6 is a block diagram illustrating an example of a functional configuration of a motor controller according to the first embodiment.

A functional configuration of the motor controller 200 for executing the brake release control and the brake engagement control according to the first embodiment described above will be described with reference to FIG. 6. FIG. 6 is a block diagram illustrating an example of a functional configuration of the motor controller 200 according to the first embodiment. Note that, in FIG. 6, the actuator 300 is also illustrated in addition for the sake of explanation.

Referring to FIG. 6, the motor controller 200 is provided with a current value computation section 201, a motor control section 203, and a brake control section 205 as functions thereof. These functions may be realized by having a processor included in the motor controller 200 conduct computational processing following a predetermined program.

The motor control section 203 controls the driving of the motor 310 of the actuator 300. The brake control section 205 controls the driving of the brake 370 of the actuator 300.

The current value computation section 201 acquires a measurement value from the torque sensor 380 of the actuator 300, and, on the basis of the measurement value, computes a current value to be given to the motor 310 in the current tracking control. In other words, on the basis of a measurement value of the torque sensor 380, the current value computation section 201 computes a torque value that the motor 310 of the actuator 300 should output to maintain the current position and attitude of the arm section 420, and uses a torque constant to compute a current value to be supplied to the motor 310 to output the torque value.

During the brake release control, the series of processes illustrated in FIG. 4 described above is executed by the current value computation section 201, the motor control section 203, and the brake control section 205. Namely, when a command to release the brake 370 and drive the actuator 300 in accordance with the control during regular operation is input (corresponding to the process in step S101), a measurement value of the torque sensor 380 is acquired and a current value for the current tracking control is computed by the current value computation section 201 (corresponding to the process in step S103).

Subsequently, on the basis of the current value computed by the current value computation section 201, the motor control section 203 drives the motor 310, thereby causing the current tracking control to be conducted (corresponding to the process in step S105). Information indicating that the current tracking control has been started is provided from the motor control section 203 to the brake control section 205, and the brake control section 205 starts the release of the brake 370 (corresponding to the process in step S107).

Subsequently, after the fixed time elapses (corresponding to the process in step S109), the motor control section 203 switches the control of the motor 310 from the current tracking control to the control during regular operation (corresponding to the process in step S111). During regular operation, the motor control section 203 drives the motor 310 in accordance with a control quantity required in accordance with a method of position control or force control in the control system 100 illustrated in FIG. 3.

Also, during the brake engagement control, the series of processes illustrated in FIG. 5 described above is executed by the current value computation section 201, the motor control section 203, and the brake control section 205. Namely, when a command to stop the control during regular operation in the actuator 300 and lock the joint section with the brake 370 is input (corresponding to the process in step S201), a measurement value of the torque sensor 380 is acquired and a current value for the current tracking control is computed by the current value computation section 201 (corresponding to the process in step S203).

Subsequently on the basis of the current value computed by the current value computation section 201, the motor control section 203 drives the motor 310, thereby causing the current tracking control to be conducted (corresponding to the process in step S205). Information indicating that the current tracking control has been started is provided from the motor control section 203 to the brake control section 205, and the brake control section 205 starts the locking of the rotating shaft by the brake 370 (corresponding to the process in step S107).

Subsequently, after the fixed time elapses (corresponding to the process in step S209), the motor control section 203 stops the supply of current to the motor 310 (that is, stops the current tracking control) (corresponding to the process in step S211).

The above thus describes a functional configuration of the motor controller 200 with reference to FIG. 6.

(3. Second Embodiment)

A second embodiment of the present disclosure will be described. In the second embodiment, in addition to the brake release control and the brake engagement control, a process of detecting an abnormality of the motor 310 or the brake 370 is conducted.

Note that the second embodiment is similar to the first embodiment described above, except that a process of detecting an abnormality is conducted, and the functional configuration of the motor controller 200 is changed in association with the addition of the process. Namely, the apparatus configuration of the support arm apparatus 400, the configuration of the actuator 300, and the system configuration of the support arm apparatus 400 are similar to those in FIGS. 1 to 4. However, in the second embodiment, in the system configuration of the support arm apparatus 400 illustrated in FIG. 3, instead of the motor controller 200, a motor controller 200a that includes a function for executing various processes according to the second embodiment is provided. Consequently, in the following description of the second embodiment, the features that differ from those of the first embodiment will be described primarily, whereas detailed description of the features that overlap with those of the first embodiment will be omitted.

(3-1. Control Method)

A control method according to the second embodiment executed in the system configuration illustrated in FIG. 3 will be described. Note that each of the processes illustrated in FIGS. 7 and 8 described below corresponds to a process executed with respect to each corresponding actuator in each of the motor controllers 200a.

(3-1-1. Brake Release Control)

Figure 7:
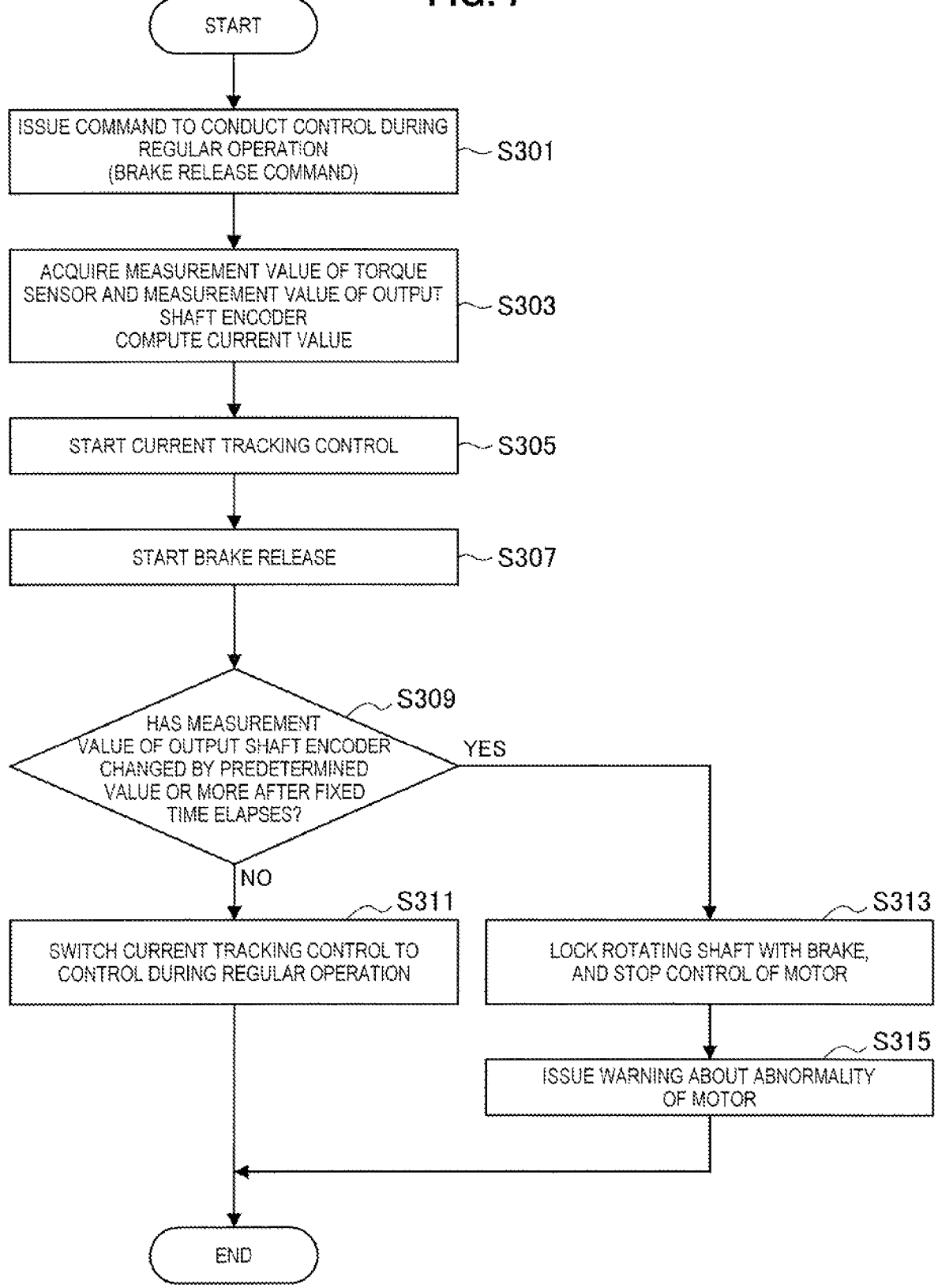
FIG. 7 is a flowchart illustrating an example of a processing procedure of a brake release control according to a second embodiment.

A processing procedure of the brake release control according to the second embodiment will be described with reference to FIG. 7. FIG. 7 is a flowchart illustrating an example of a processing procedure of the brake release control according to the second embodiment.

Note that the processing procedure of the brake release control according to the second embodiment is similar to the brake release control according to the first embodiment, up to the process in which the release of the brake 370 is started. In other words, the processes from step S301 to step S307 illustrated in FIG. 7 are similar to the processes from step S101 to step S107 illustrated in FIG. 4. Consequently, a description of each of these processes is omitted herein.

In the brake release control according to the second embodiment, when the release of the brake is started in step S307, next, it is determined whether or not a measurement value of the output shaft encoder 340 has changed by a predetermined value or more after the fixed time elapses (step S309). Herein, standing by until the fixed time elapses in step S309 is for standing by until the release of the brake 370 functions effectively, similar to the process in step S109 illustrated in FIG. 4. In other words, in the second embodiment, in the state in which the release of the brake 370 is thought to have functioned effectively, it is determined whether or not the measurement value of the output shaft encoder 340 has changed by the predetermined value or more.

At the stage illustrated in step S309, since the current tracking control is being conducted, even if the brake 370 is released, the position and the attitude of the arm section 420 should still be maintained mostly as-is. Consequently, in the case in which the measurement value of the output shall encoder 340 has not changed by the predetermined value or more in step S309, it is thought that the current tracking control is being conducted normally, that is, the motor 310 is operating normally. Thus, in this case, similarly to the first embodiment, the switching from the current tracking control to the control during regular operation is conducted (step S311).

On the other hand, in the case in which the measurement value of the output shaft encoder 340 has changed by the predetermined value or more in step S309, it is thought that the current tracking control is not being conducted normally, that is, the motor 310 is not operating normally. Consequently, in this case, control does not transition to the control during regular operation, and the flow proceeds to step S313, In step S313, the rotating shaft is locked by the brake 370, and the control of the motor 310 is stopped. If the current tracking control is continued even though an abnormality has occurred ha the motor 310, the position and the attitude of the arm section 420 cannot be maintained. For this reason, by stopping the current tracking control and engaging the brake 370, the position and the attitude of the arm section 420 are locked safely.

Additionally, the user is warned about the abnormality of the motor 310 (step S315). The warning may be a visual warning that displays text or the like on a display apparatus that displays the image taken by the imaging unit 423, and may also be an auditory warning by a buzzer, alarm, or the like, for example.

The above describes a processing procedure of the brake release control according to the second embodiment with reference to FIG. 7.

(3-1-2. Brake Engagement Control)

Figure 8:
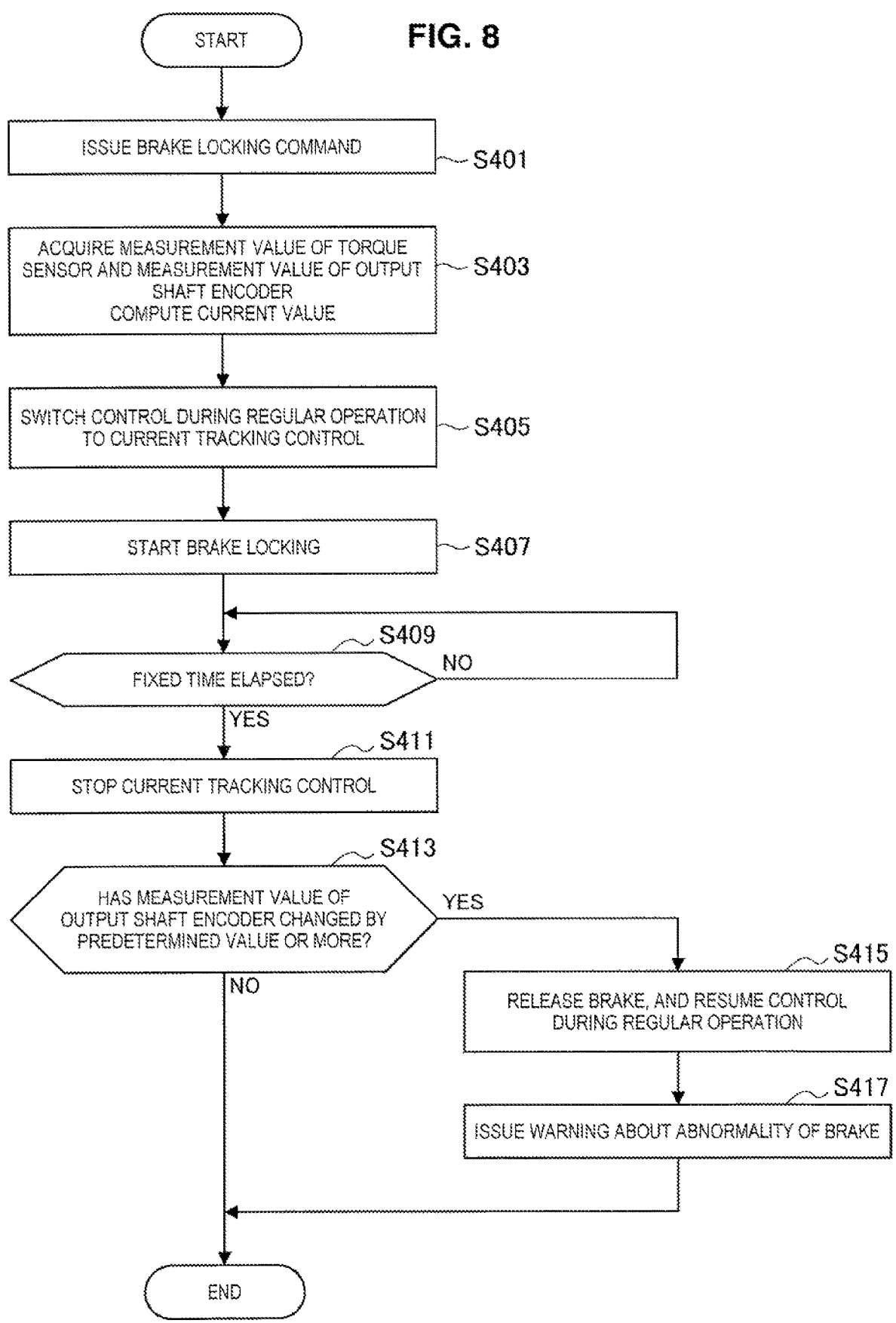
FIG. 8 is a flowchart illustrating an example of a processing procedure of a brake engagement control according to the second embodiment.

A processing procedure of the brake engagement control according to the second embodiment be described with reference to FIG. 8. FIG. 8 is a flowchart illustrating an example of a processing procedure of the brake engagement control according to the second embodiment.

Note that the brake engagement control according to the second embodiment is similar to the brake engagement control according to the first embodiment, up to the process in which the joint section is locked by the brake 370 and the current tracking control is stopped. In other words, the processes from step S401 to step S411 illustrated in FIG. 8 are similar to the processes from step S201 to step S211 illustrated in FIG. 5. Consequently, a description of each of these processes is omitted herein.

In the brake engagement control according to the second embodiment, when the current tracking control is stopped in step S411, next, it is determined whether or not the measurement value of the output shaft encoder 340 has changed by a predetermined value or more (step S413). At the stage illustrated in step S413, the position and the attitude of the arm section 420 should be locked by the functioning of the brake 370. Consequently, in the case in which the measurement value of the output shaft encoder 340 has not changed by the predetermined value or more in step S413, it is thought that the brake 370 is engaging normally, and no special process is conducted.

On the other hand, in the case in which the measurement value of the output shaft encoder 340 has changed by the predetermined value or more in step S413, it is thought that the brake 370 is not engaging normally. Consequently, in this case, the flow proceeds to step S415, the brake 370 is released, and the control during regular operation is resumed. In this case, since the brake 370 is in a state of being unable to lock the position and the attitude of the arm section 420, by transitioning to the control during regular operation, the position and the attitude of the arm section 420 are maintained safely by the driving force of the motor 310.

Additionally, the user is warned about the abnormality of the brake 370 (step S417). The warning may be a visual warning that displays text or the like on a display apparatus that displays the image taken by the imaging unit 423, and may also be an auditory warning by a buzzer, alarm, or the like, for example.

The above describes a processing procedure of the brake engagement control according to the second embodiment with reference to FIG. 8.

As described above, according to the second embodiment, in the middle of the brake release control and the brake engagement control, an abnormality of the motor 310 or the brake 370 is detected on the basis of the measurement value of the output shaft encoder 340. Specifically, in the case in which the measurement value of the output shaft encoder 340 changes greatly while releasing the brake 370, an abnormality of the motor 310 is detected, and the position and the attitude of the arm section 420 are locked safely by the brake 370. Also, in the case in which the measurement value of the output shaft encoder 340 changes greatly while locking the rotating shaft with the brake 370, an abnormality of the brake 370 is detected, and the position and the attitude of the arm section 420 are locked safely by the driving force of the motor 310.

In this way, according to the second embodiment, in addition to the effects obtained in the first embodiment, there is exhibited a further effect by which a safer support arm apparatus 400 may be provided.

Also, this is because, as described above, in the actuator 300, due to backlash of the speed reducer 320, strain of the torque sensor 380, and the like, there is a possibility that the measurement value of the input shaft encoder 330 does not necessarily indicate the rotational angle of the output shaft 350 accurately. Consequently, in the second embodiment, like in the examples illustrated in FIGS. 7 and 8, by detecting an abnormality of the motor 310 or the brake 370 using a measurement value of the output shaft encoder 340 rather than a measurement value of the input shaft encoder 330, the abnormality can be detected with higher accuracy.

(3-2. Functional Configuration of Motor Controller)

Figure 9:
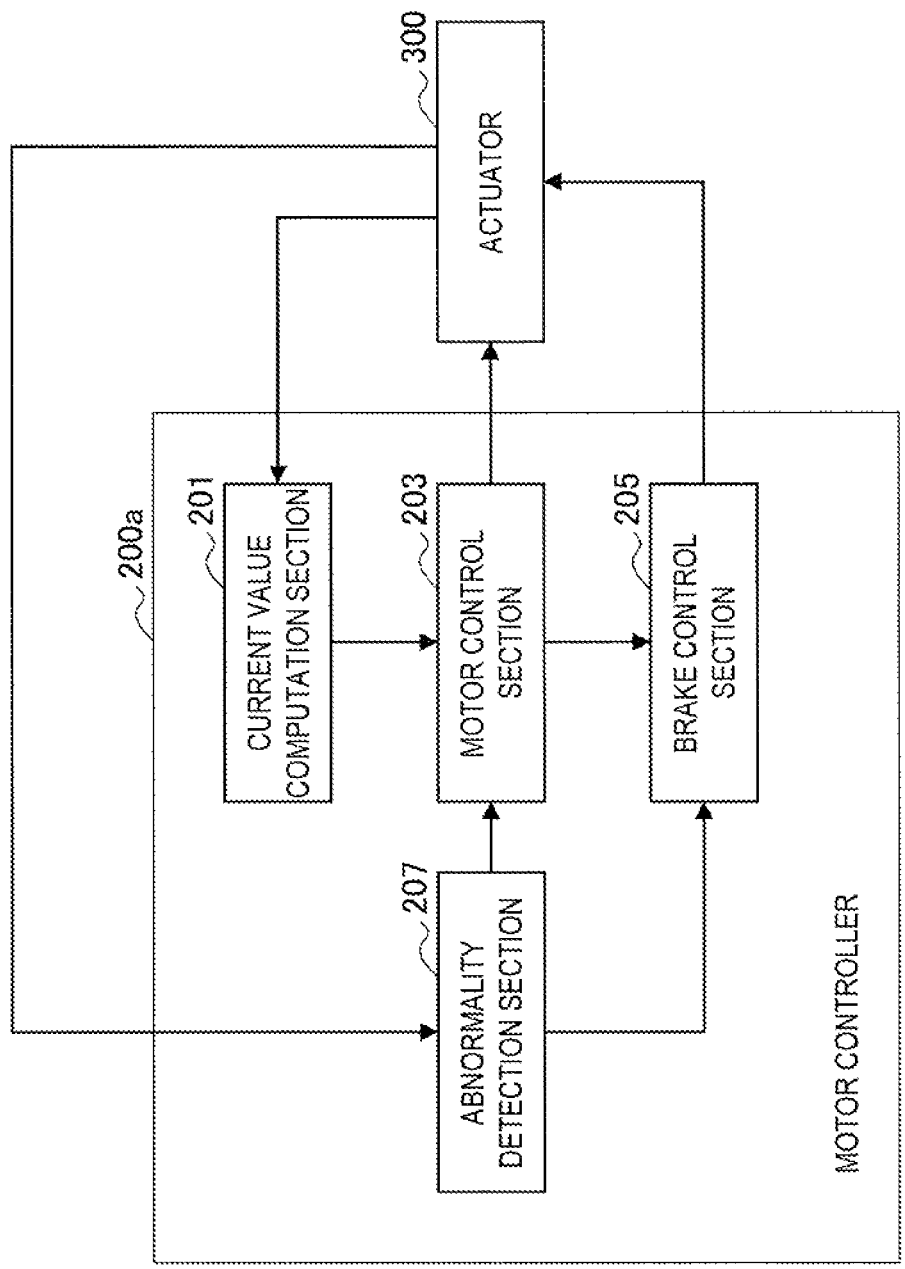
FIG. 9 is a block diagram illustrating an example of a functional configuration of a motor controller according to the second embodiment.

A functional configuration of the motor controller 200a for executing the brake release control and the brake engagement control according to the second embodiment described above will be described with reference to FIG. 9. FIG. 9 is a block diagram illustrating an example of a functional configuration of the motor controller 200a according to the second embodiment. Note that, in FIG. 9, the actuator 300 is also illustrated in addition for the sake of explanation.

Referring to FIG. 9, the motor controller 200a is provided with a current value computation section 201, a motor control section 203, a brake control section 205, and an abnormality detection section 207 as functions thereof. These functions may be realized by having a processor included in the motor controller 200a conduct computational processing following a predetermined program. Note that the functions of the current value computation section 201, the motor control section 203, and the brake control section 205 are substantially similar to these functions in the motor controller 200 according to the first embodiment described with reference to FIG. 6, and thus a detailed description will be omitted herein.

The abnormality detection section 207 acquires a measurement value from the output shaft encoder 340 of the actuator 300, and on the basis of the measurement value, detects an abnormality of the motor 310 or the brake 370.

Specifically, in the case in which the measurement value of the output shaft encoder 3-10 changes greatly while releasing the brake 370, the abnormality detection section 207 determines that an abnormality is occurring in the motor 310, and, through the motor control section 203 and the brake control section 205, engages the brake 370 while also stopping the control of the motor 310 (corresponding to the process in step S313). Furthermore, the abnormality detection section 207 issues a warning indicating that an abnormality of the motor 310 has been detected (corresponding to the process in step S313).

Also, in the case in which the measurement value of the output shaft encoder 340 changes greatly while locking the rotating shaft with the brake 370, the abnormality detection section 207 determines that an abnormality is occurring in the brake 370, and, through the motor control section 203 and the brake control section 205, releases the brake 370 while also starting the control of the motor 310 (corresponding to the process in step S415). Furthermore, the abnormality detection section 207 issues a. warning indicating that an abnormality of the brake 370 has been detected (corresponding to the process in step S417).

The above describes a functional configuration of the motor controller 200a with reference to FIG. 9.

(4. Modifications)

The brake release control and the brake engagement control according to the first and second embodiments described above are conducted for each actuator 300 by the motor controller 200 or 200a provided in each actuator 300. For example, in the first and second embodiments, the brake release control or the brake engagement control may be conducted at the same time in each actuator 300.

However, by appropriately controlling the timings at which these controls are conducted in each actuator 300, the amount of change in the position and the attitude of the arm section 420 can be suppressed further. Herein, as a modification of the present embodiment, such an embodiment in which the brake release control or the brake engagement control is conducted at a different timing in each actuator 300 will be described.

Figure 10:
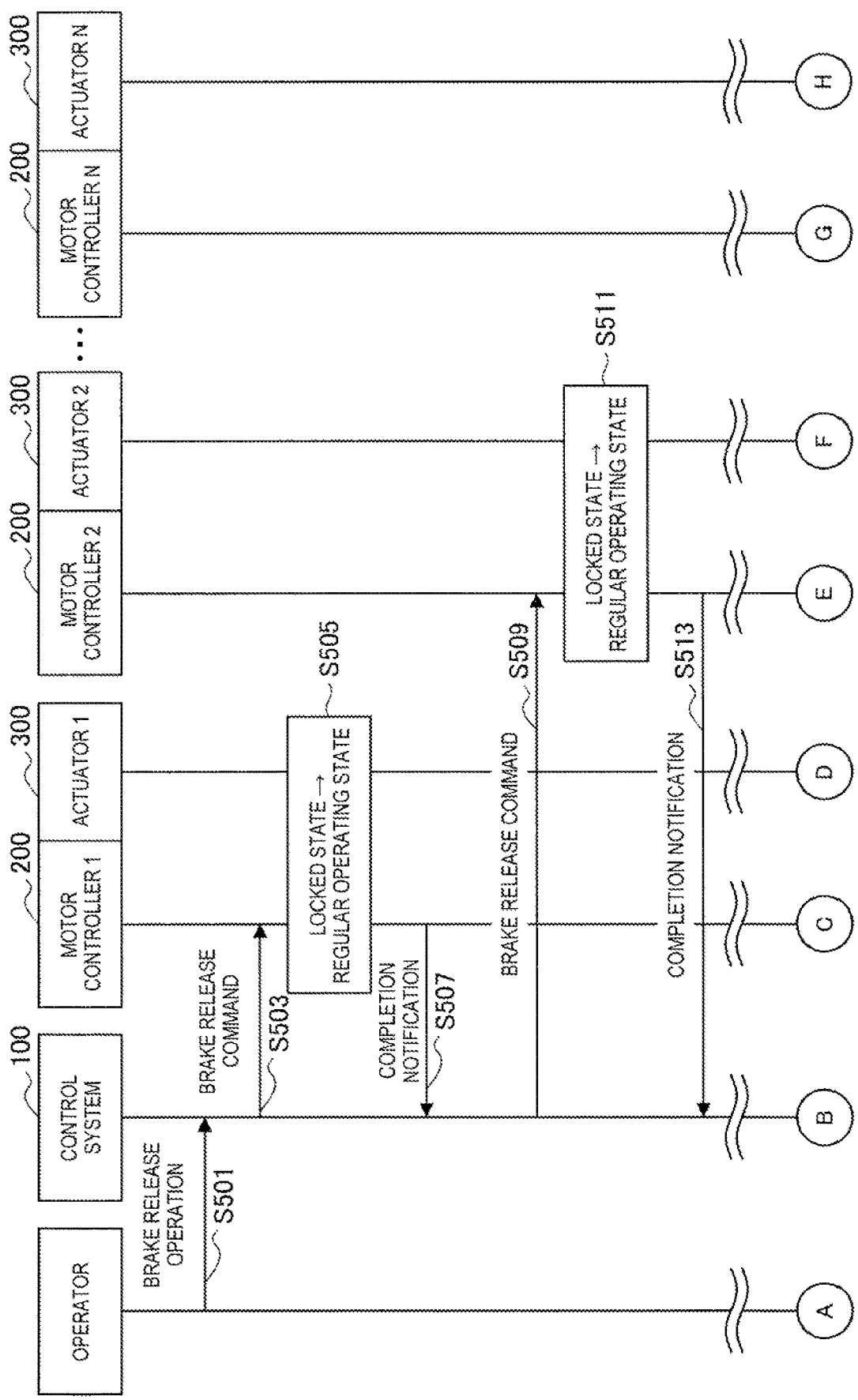
FIG. 10 is a sequence diagram illustrating a processing procedure for a modification in which the brake release control or the brake engagement control in each actuator is conducted at a different timing.
Figure 11:
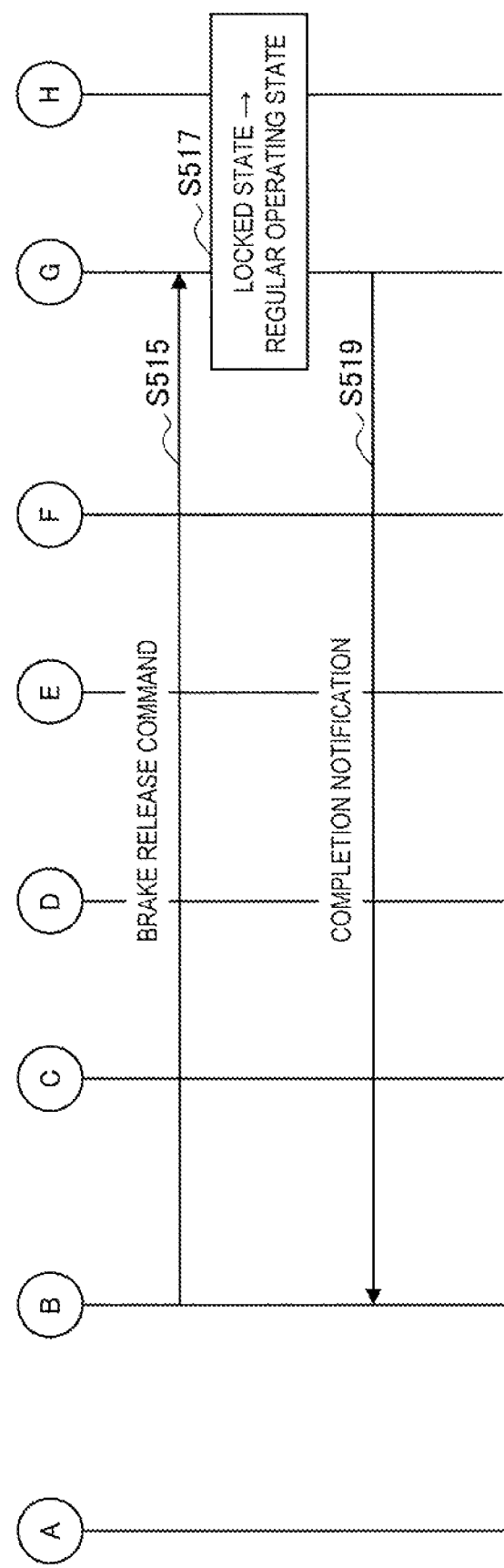
FIG. 11 is a sequence diagram illustrating an example of a processing procedure for a modification in which the brake release control or the brake engagement control in each actuator is conducted at a different timing.

FIGS. 10 and 11 are sequence diagrams illustrating an example of a processing procedure for a modification in which the brake release control or the brake engagement control in each actuator 300 is conducted at a different timing. Note that, in FIGS. 10 and 11, sequence diagrams for the case of conducting the brake release control according to the first embodiment in each actuator 300 are illustrated as one example, but the processing procedure may also be similar for the case in which another control is conducted.

Referring to FIGS. 10 and 11, in the present modification, when an operator performs a brake release operation, information indicating that the brake release operation has been performed is input into the control system 100 (step S501). Subsequently, the control system 100 does not transmit a brake release command to all of the motor controllers 200 at the same time, but instead transmits the brake release command to a certain one (in the illustrated example, Motor Controller 1) of the motor controllers 200 (step S503).

The motor controller 200 receiving the brake release command executes the series of processes (that is, the brake release control) illustrated in FIG. 4 on the actuator 300 corresponding to itself, thereby switching its state from the locked state to the regular operating state (step S505).

When the state of the actuator 300 is switched to the regular operating state by the brake release control, the motor controller 200 transmits a notification indicating that the brake release control has completed to the control system 100 (step S507).

The control system 100 receiving the notification transmits the brake release command to another (in the illustrated example, Motor Controller 2) of the motor controllers 200 (step S509). The motor controller 200 receiving the brake release command similarly executes the series of processes (that is, the brake release control) illustrated in FIG. 4 on the actuator 300 corresponding to itself, thereby switching its state from the locked state to the regular operating state (step S511). Subsequently, when the state of the actuator 300 is switched to the regular operating state, the motor controller 200 transmits a notification indicating that the brake release control has completed to the control system 100 (step S513).

Similarly thereafter, the brake release control is conducted successively on the N actuators 300 included in the support arm apparatus 400 (step S515 to step S519).

In the above example, the case of conducting the brake release control is described, but the same applies to the case of conducting the brake engagement control. In this way, in the present modification, the brake release control or the brake engagement control is conducted at a different timing on each actuator 300 included in the support arm apparatus 400.

Herein, in the support arm apparatus 400, the position of the front end of the arm section 420 is decided by the attitude of all of the joint sections. Consequently, in the case in which the brake release control or the brake engagement control is conducted at the same time in all of the joint sections, the amounts of change of each of the joint sections become accumulated more going towards the front end, and the amount of change of the position becomes greater. Also, in the case in which shaking is produced by sympathetic vibration or the like when releasing the brake 370 or starting the control of the motor 310, in the torque sensors 380 and the output shaft encoders 340 of the other joint sections, the shaking is detected as noise, and there is a risk of influencing the control of the arm section 420.

Accordingly, in the present modification, the brake release control or the brake engagement control in each actuator 300 is executed at an appropriate timing so that the shaking or the like produced by the brake release control or the brake engagement control in each actuator 300 of each joint section influences the other joint sections as little as possible. With this arrangement, changes in the position and the attitude of the front end (that is, the imaging unit 423) of the arm section 420 can be kept to a minimum.

For example, the timing of executing the brake release control or the brake engagement control may be set appropriately with consideration for how easily shaking is produced in the arm section 420 when executing the brake release control or the brake engagement control. How easily shaking is produced in each joint section may be predicted from the configuration of the arm section 420 (such as the arrangement of the joint sections, the length of each link, and the inertia of each joint section). For example, shaking produced in a relatively long link when conducting the brake release control or the brake engagement control in a joint section connected to the link is thought to be greater as compared to the case in which the link is short. Consequently, the timing, of executing the brake release control or the brake engagement control in each actuator 300 may be set on the basis of the configuration of the arm section 420.

Also, how easily shaking is produced in the arm section 420 is also thought to change depending on the attitude of the arm section 420 when attempting to conduct the brake release control or the brake engagement control. Consequently, the control system 100 may also detect the attitude of the arm section 420 on the basis of the measurement value of the output shaft encoder 340 and the measurement value of the torque sensor 380 of each actuator 300, and, on the basis of the detected attitude, decide the timing at which to execute the brake release control or the brake engagement control in each actuator 300.

As an example, to further reduce changes in the position and the attitude of the front end (that is, the imaging unit 423) of the arm section 420, the brake release control or the brake engagement control may be executed favorably in order from the joint section (actuator 300) on the front end side of the arm section 420. This is because, although shaking produced in a joint section closer to the base end side disposed at a position farther away from the front end is thought to have a greater influence on the front end, if the brake release control or the brake engagement control in a joint section close to the front end has already finished when the brake release control or the brake engagement control is conducted in a joint section on the base end side, the influence on the front end of the arm section 420 exerted by shaking or the like in a joint section on the base end side is thought to become smaller.

Herein, to transmit the brake release command to each motor controller 200 according to a preset order and timing, it is necessary to ascertain the completion of the brake release control in each motor controller 200. In the above example, the control system 100 ascertains the completion of the brake release control in each motor controller 200 by receiving a completion notification from each motor controller 200. However, the method by which the control system 100 ascertains the completion of the brake release control (or the brake engagement control) in each motor controller 200 is not limited to such an example.

For example, after transmitting the brake release command or the brake engagement command to the single motor controller 200, the control system 100 may stand by for a predetermined time at which the brake release control or the brake engagement control is predicted to complete, treat the brake release control or the brake engagement control as being complete by the elapsing of the predetermined time, and transmit the brake release command or the brake engagement command to the next motor controller 200 according to the preset order and timing. Alternatively, after transmitting the brake release command or the brake engagement command to the single motor controller 200, the control system 100 may acquire the measurement value of the output shaft encoder 340 and the measurement value of the torque sensor 380 of the actuator 300 corresponding to the motor controller 200, and after sensing on the basis of these measurement values that the brake release control or the brake engagement control has completed, and then transmit the brake release command or the brake engagement command to the next motor controller 200 according to the preset order and timing.

(5. Experiment Results)

To confirm the advantageous effects of the present disclosure, the brake release control according to the first embodiment described above was actually executed in an support arm apparatus, and the amount of change in the rotational angle of the output shaft in the actuator at the time and the driving current value of the motor (the current value given to the motor while driving) were measured. Note that the support arm apparatus used in the experiment includes an arm section configured to have six degrees of freedom, with actuators provided in the joint shafts, similarly to the support arm apparatus 400 illustrated in FIG. 1. Also, the actuator provided in each joint section is an actuator with a. built-in brake, having a configuration substantially similar to the actuator 300 illustrated in FIG. 3.

Figure 12:
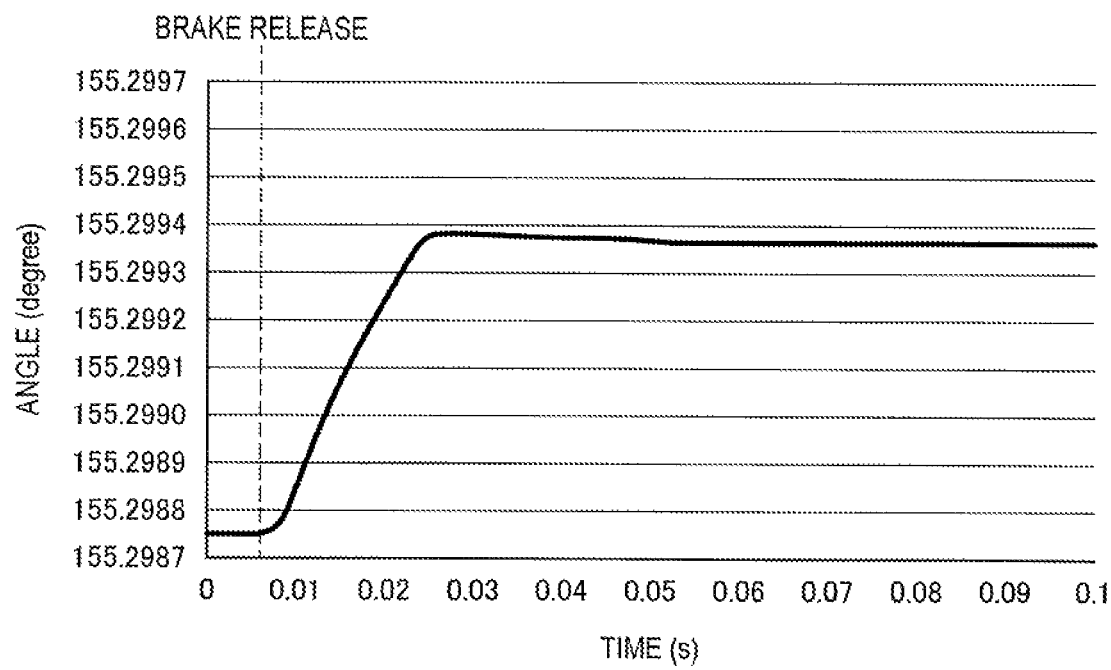
FIG. 12 is a g graph illustrating change in a rotational angle of an output shaft of an actuator when the brake release control is executed.
Figure 13:
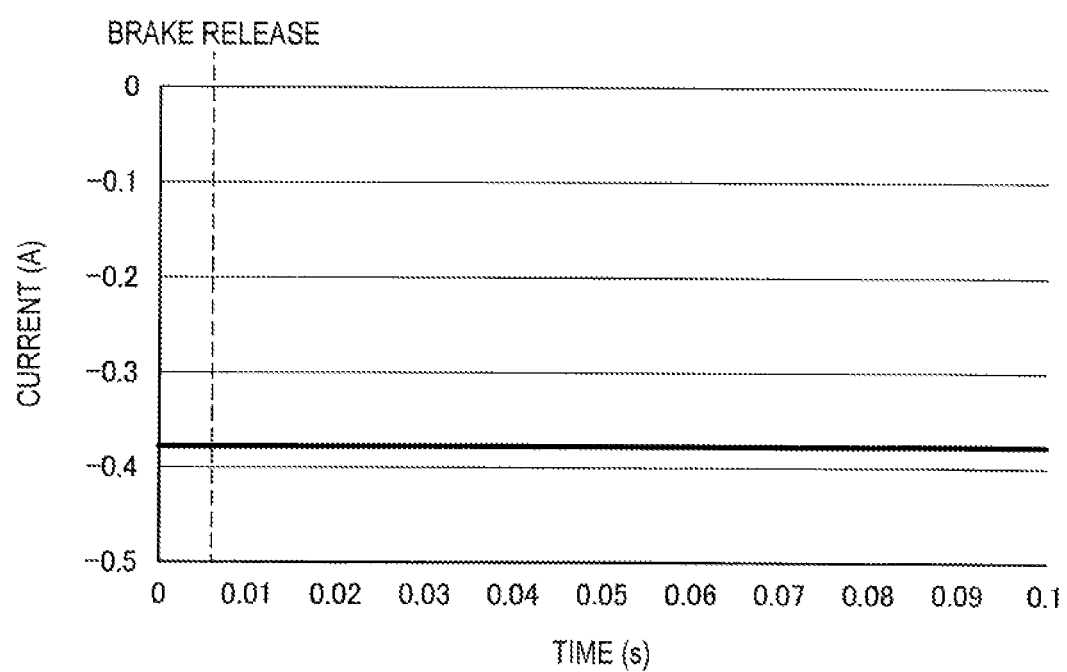
FIG. 13 is a graph illustrating change in a driving current of a motor of an actuator when the brake release control is executed.

The measurement results are illustrated in FIGS. 12 and 13. FIG. 12 is a graph illustrating change in the rotational angle of the output shaft of the actuator when the brake release control is executed. FIG. 13 is a graph illustrating change in the driving current of the motor of the actuator when the brake release control is executed.

FIG. 12 takes time as the horizontal axis, takes the rotational angle of the output shaft of the actuator measured by the output shaft encoder as the vertical axis, and illustrates the change over time in the rotational angle. Also, FIG. 13 takes time as the horizontal axis, takes the driving current of the motor of the actuator as the vertical axis, and illustrates the change over time in the driving current. Also, both FIGS. 12 and 13 use a dashed line to indicate the timing (time) at which the release of the brake of the actuator is started.

Referring to FIG. 13, it can be confirmed that, from before the release of the brake is started, the motor is being driven by a near-constant current value, that is, the current tracking control is being conducted. Also, referring to FIG. 12. it is demonstrated that, by releasing the brake, the rotational angle of the output shaft changes slightly, but the amount of change is less than 0.001° and is kept extremely small.

In this way, from the results illustrated in FIGS. 12 and 13, it can be confirmed that, by conducting the current tracking control from before the release of the brake is started, it is possible to effectively suppress angle changes in the output shaft of the actuator attendant on the release of the brake.

(6. Supplement)

The preferred embodiments of the present disclosure have been described above with reference to the accompanying drawings, whilst the present disclosure is not limited to the above examples, of course. A person skilled in the art may find various alterations and modifications within the scope of the appended claims, and it should be understood that they will naturally come under the technical scope of the present disclosure.

In addition, the effects described in the present specification are merely illustrative and demonstrative, and not limitative. In other words, the technology according to the present disclosure can exhibit other effects that are evident to those skilled in the art along with or instead of the effects based on the present specification.

For example, in the foregoing embodiment, the control target is taken to be the arm section 420 having a configuration in which the actuators 300 are provided in all of the joint sections 421*a* to 421*f*, but the present technology is not limited to such an example. For example, the brake release control and the brake engagement control described above may also be applied to an arm section in which actuators is provided only in some joint sections (also known as an arm section that includes a passive shaft). In this case, the brake release control and the brake engagement control are executed only with respect to the joint sections provided with the actuators.

Additionally, the present technology may also be configured as below.

(1)

A control apparatus configured to execute a current tracking control on a basis of a measurement value of a torque sensor of an actuator provided in at least one of multiple joint sections included in an arm section of as medical support arm apparatus, the current tracking control causing a motor of the actuator to output torque by which a position and an attitude of the arm section are maintained, and switch a first state in which the motor is driven in accordance with a predetermined control method, and a second state in which the joint section is locked using a brake of the actuator.

(2)

The control apparatus according to (1), in which the actuator is an actuator with a built-in brake, the actuator having the brake attached to an input shaft.

(3)

The control apparatus according to (1) or (2), in which the actuator includes an encoder that measures a rotational angle of a drive shaft of the motor, and the control apparatus decides a timing at which to end the current tracking control on a basis of a measurement value of the encoder.

(4)

The control apparatus according to any one of (1) to (3), in which the actuator includes an encoder that measures a rotational angle of a drive shaft of the motor, and the control apparatus detects an abnormality of the motor or the brake on a basis of a measurement value of the encoder.

(5)

The control apparatus according to (4), in which the control apparatus detects an abnormality of the motor on a basis of a measurement value of the encoder while the brake is being released.

(6)

The control apparatus according to (4), in which the control apparatus detects an abnormality of the brake on a basis of a measurement value of the encoder when the joint section is being locked by the brake.

(7)

The control apparatus according to any one of (3) to (6), in which the encoder is an output shaft encoder that measures a rotational angle of an output shaft through a speed reducer of the motor (8)

The control apparatus according to any one of (1) to (7), in which in the current tracking control, a current value supplied to the motor to cause the motor to output predetermined torque is computed for each motor by using a torque constant unique to the motor of each joint section.

(9)

The control apparatus according to any one of (1) to (8), in which the control apparatus executes the switching between the first state and the second state at mutually different timings for each joint section.

(10)

The control apparatus according to (9), in which the timing of switching between the first state and the second state for each joint section is decided on a basis of at least one of a configuration of the arm section, and the position and the attitude of the arm section when switching states.

(11)

The control apparatus according to any one of (1) to (10), in which a medical tool used in a medical procedure is provided on a front end of the arm section.

(12)

The control apparatus according to (11), in which the medical tool is an imaging unit for imaging and performing enlarged observation of an operative site of a patient.

(13)

A control method including:

executing a current tracking control on a basis of a measurement value of a torque sensor of an actuator provided in at least one of multiple joint sections included in an arm section of a medical support am apparatus, the current tracking control causing a motor of the actuator to output torque by which a position and an attitude of the arm section are maintained: and switching a first state in which the motor is driven in accordance with a predetermined control method, and a second state in which the joint section is locked using a brake of the actuator.

(14)

A medical support arm apparatus including:

an arm section provided a medical tool on a front end; and a control apparatus configured to control an operation of the arm section, in which the control apparatus is configured to execute a current tracking control on a basis of a measurement value of a torque sensor of an actuator provided in at least one of multiple joint sections included in the arm section, the current tracking control causing a motor of the actuator to output torque by which a position and an attitude of the arm section are maintained, and switch a first state in which the motor is driven in accordance with a predetermined control method, and a second state in which the joint section is locked using a brake of the actuator.

REFERENCE SIGNS LIST

100 control system
110 user interface
200, 200a. motor controller
201 current value computation section
203 motor control section
205 brake control section
207 abnormality detection section
300 actuator
310 motor
320 speed reducer
330 input shaft encoder
340 output shaft encoder
350 output shaft
360 housing
370 brake
380 torque sensor
400 support arm apparatus (observation apparatus)
410 base section
420 arm section
421a to 421f joint section
423 imaging unit
430 control apparatus

The invention claimed is:

1. A control apparatus, comprising
circuitry configured to
execute a current tracking control based on a torque of an actuator in at least one joint section of multiple joint sections in an arm section of a medical support arm apparatus, the current tracking control causing a motor of the actuator to output torque to maintain a position and an attitude of the arm section, and
during the current tracking control, switch between a first state in which the motor is driven in accordance with a predetermined control method and a second state in which the joint section is locked using a brake of the actuator, wherein
the actuator includes an encoder that measures a rotational angle of a drive shaft of the motor, and
the circuitry is configured to detect an abnormality of the motor or the brake on a based on the rotational angle.

2. The control apparatus according to claim 1, wherein the actuator is an actuator with a built-in brake, the actuator having the brake attached to an input shaft.

3. The control apparatus according to claim 1, wherein the circuitry is configured to decide a timing at which to end the current tracking control based on the rotational angle.

4. The control apparatus according to claim 1, wherein the circuitry is configured to detect an abnormality of the motor based on the rotational angle while the brake is being released.

5. The control apparatus according to claim 1, wherein the circuitry is configured to detect an abnormality of the brake based on the rotational angle when the at least one joint section is being locked by the brake.

6. The control apparatus according to claim 3, wherein the encoder is an output shaft encoder that measures a rotational angle of an output shaft through a speed reducer of the motor.

7. The control apparatus according to claim 1, wherein
in the current tracking control, the circuitry is configured to compute a current value for each motor using a torque constant unique to each motor of each joint section and supply the current value to each motor.

8. The control apparatus according to claim 1, wherein
the circuitry is configured to switch between the first state and the second state at mutually different timings for each joint section.

9. The control apparatus according to claim 8, wherein
the circuitry is configured to decide timing of switching between the first state and the second state for each joint section based on at least one of a configuration of the arm section, and the position and the attitude of the arm section when switching states.

10. The control apparatus according to claim 1, wherein
a medical tool used in a medical procedure is provided on a front end of the arm section.

11. The control apparatus according to claim 10, wherein
the medical tool is an imaging unit for imaging and performing enlarged observation of an operative site of a patient.

12. The medical support arm apparatus according to claim 1, wherein
the encoder is an output shaft encoder that measures a rotational angle of an output shaft through a speed reducer of the motor.

13. A control method, comprising:
executing a current tracking control based on a torque of an actuator in at least one joint section of multiple joint sections included in an arm section of a medical support arm apparatus, the current tracking control causing a motor of the actuator to output torque maintain a position and an attitude of the arm section;
during the current tracking control, switching between a first state in which the motor of the actuator is driven in accordance with a predetermined control method and a second state in which the at least one joint section is locked using a brake of the actuator, wherein the actuator includes an encoder that measures a rotational angle of a drive shaft of the motor; and
detecting an abnormality of the motor or the brake on a based on the rotational angle.

14. A medical support arm apparatus, comprising:
an arm section including on a front end to which a medical tool is to be secured; and
control circuitry configured to control an operation of the arm section, wherein the control circuitry is configured to
execute a current tracking control based on a torque an actuator provided in at least one joint section of multiple joint sections included in the arm section, the current tracking control causing a motor of the actuator to output torque to maintain a position and an attitude of the arm section, and
during the current tracking control, switch between a first state in which the motor is driven in accordance with a predetermined control method and a second state in which the at least one joint section is locked using a brake of the actuator, wherein
the actuator includes an encoder that measures a rotational angle of a drive shaft of the motor, and
the control circuitry is configured to detect an abnormality of the motor or the brake on a based on the rotational angle.

15. The medical support arm apparatus according to claim 14, wherein
the actuator is an actuator with a built-in brake, the actuator having the brake attached to an input shaft.

16. The medical support arm apparatus according to claim 14, wherein
the control circuitry is configured to decide a timing at which to end the current tracking control based on the rotational angle.

17. The medical support arm apparatus according to claim 16, wherein
the encoder is an output shaft encoder that measures a rotational angle of an output shaft through a speed reducer of the motor.

18. The medical support arm apparatus according to claim 14, wherein
the encoder is an output shaft encoder that measures a rotational angle of an output shaft through a speed reducer of the motor.

* * * * *